(12) United States Patent
Aaronson et al.

(10) Patent No.: US 9,084,868 B2
(45) Date of Patent: Jul. 21, 2015

(54) SAFETY URINARY CATHETER

(71) Applicant: The Regents of the University of California, Oakland, CA (US)

(72) Inventors: David Aaronson, San Francisco, CA (US); Sarah Blaschko, San Francisco, CA (US); Maurice Garcia, San Francisco, CA (US); Alex Wu, San Francisco, CA (US)

(73) Assignee: The Regents of the University of California, Oakland ( * ) Notice: Subject to any disclaimer, the term of this patent is extended or adjusted under 35 U.S.C. 154(b) by 4 days.

(21) Appl. No.: 13/737,563

(22) Filed: Jan. 9, 2013

(65) Prior Publication Data
US 2013/0197486 A1     Aug. 1, 2013

Related U.S. Application Data

(63) Continuation of application No. PCT/US2011/043587, filed on Jul. 11, 2011.

(60) Provisional application No. 61/363,169, filed on Jul. 9, 2010.

(51) Int. Cl.
| A61M 27/00 | (2006.01) |
| A61M 25/00 | (2006.01) |
| A61M 39/24 | (2006.01) |

(52) U.S. Cl.
CPC ........... *A61M 25/0017* (2013.01); *A61M 25/00* (2013.01); *A61M 25/008* (2013.01); *A61M 25/0074* (2013.01); *A61M 2039/2426* (2013.01)

(58) Field of Classification Search
CPC ............ A61M 25/00; A61M 25/0017; A61M 25/0074; A61M 25/0075; A61M 25/008; A61M 25/01; A61M 25/02; A61M 25/04; A61M 25/10; A61M 25/10184; A61M 25/10185; A61M 2025/0074; A61M 2025/0075; A61M 2025/1018; A61M 2025/1093; A61M 2210/1078; A61M 2210/1085; A61M 2210/1089; A61M 2039/2426

See application file for complete search history.

(56) References Cited

U.S. PATENT DOCUMENTS

| 3,543,758 | A | 12/1970 | McWhorter |
| 3,543,759 | A | 12/1970 | McWhorter |
| 3,924,634 | A | 12/1975 | Taylor et al. |
| 4,264,312 | A * | 4/1981 | Cianci ........................ 434/262 |
| 5,919,170 | A | 7/1999 | Woessner |
| 6,283,940 | B1 | 9/2001 | Mulholland |
| 7,883,503 | B2 | 2/2011 | Kaiser et al. |
| 8,382,708 | B2 | 2/2013 | Mayback et al. |
| 8,500,684 | B2 * | 8/2013 | Gardner et al. ............ 604/99.04 |
| 2002/0198506 | A1 * | 12/2002 | Whalen et al. ................ 604/328 |
| 2004/0199086 | A1 | 10/2004 | Crisp |
| 2006/0167438 | A1 | 7/2006 | Kalser et al. |

(Continued)

OTHER PUBLICATIONS

International Search Report and Written Opinion mailed Feb. 29, 2012 for PCT Patent Application No. PCT/US2011/043587, 11 pages.

*Primary Examiner* — Leslie Deak
*Assistant Examiner* — Kai Weng
(74) *Attorney, Agent, or Firm* — Mintz Levin Cohn Ferris Glovksy and Popeo PC

(57) ABSTRACT

There is provided, inter alia, a catheter incorporating one or more of a burstable element, a safety balloon, a marking to indication proper insertion amount for the catheter, a slit valve, and a non-fragmenting retention balloon

2 Claims, 7 Drawing Sheets

(56) References Cited

U.S. PATENT DOCUMENTS

| | | |
|---|---|---|
| 2008/0033570 A1 | 2/2008 | Blitz et al. |
| 2010/0106142 A1* | 4/2010 | Bolmsjo et al. ............... 604/544 |
| 2012/0101515 A1 | 4/2012 | Barbod |

* cited by examiner

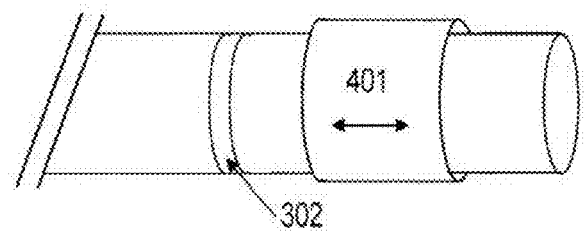
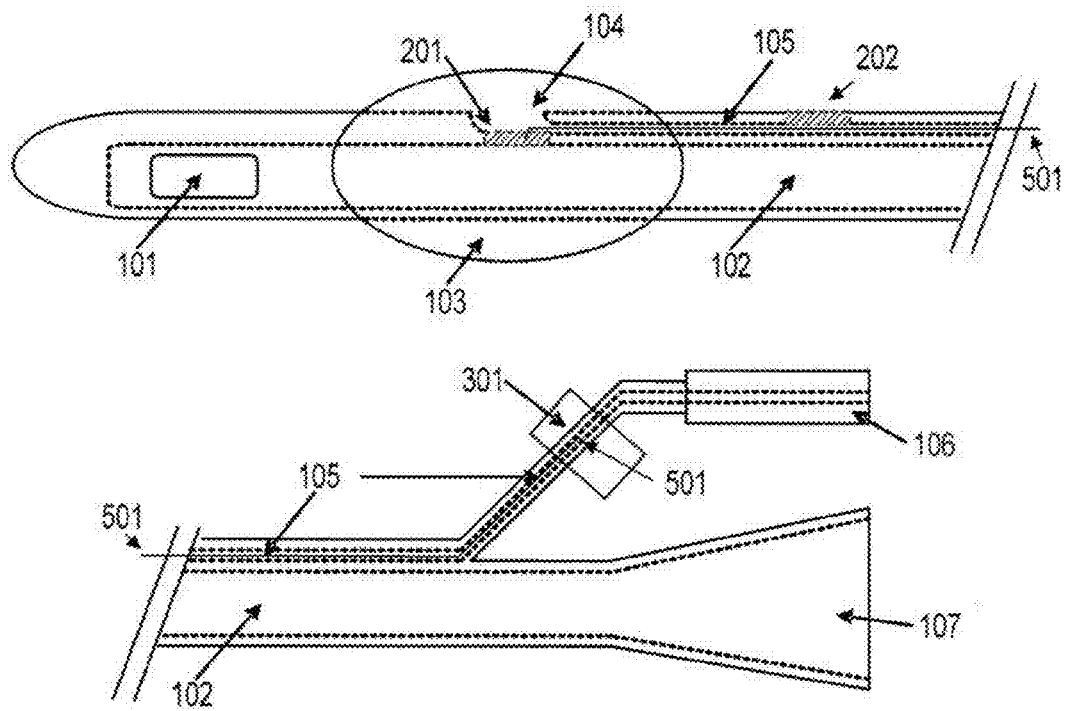
FIG.4
FIG.5

SAFETY URINARY CATHETER

CROSS-REFERENCE TO RELATED APPLICATION

This application is a continuation of International Application No. PCT/US2011/043587, filed Jul. 11, 2011, which claims the benefit of U.S. Provisional Application No. 61/363,169, filed Jul. 9, 2010, the entire contents of each of which are incorporated herein by reference in its entirety and for all purposes.

BACKGROUND OF THE INVENTION

Catheters are used in a variety of applications in medicine including, for example, employing a so-called "urinary catheter" relating to draining the urinary bladder. Typically, a urinary catheter is placed through the urethra into the bladder of a subject for a variety of medical indications including relief of urinary obstruction, monitoring urine output, prevention of urinary incontinence, and the like as known in the art. Indwelling urinary catheters, designed to remain in place to drain the bladder, include at least two tubes running in parallel substantially through the length of the catheter without fluid communication between the tubes. At the distal end of a urinary catheter is a hole for urine inflow and drainage connected to one of the tubes (i.e., the so-called "drainage tube") which can terminate at a "drainage port," and a balloon that can be filled to secure the urinary catheter. The balloon can be filled with liquid through the other tube (i.e., the so-called "balloon tube") which can terminate at a "balloon port." As known in the art, each tube can terminate outside the body, or each tube can terminate within the body depending on the specific medical application. For example, the drainage tube can be linked to a urine collection bag. The balloon tube has a valve allowing instillation or removal of liquid into or from the balloon (e.g., with a syringe). As known in the art, the purpose of the inflated balloon is to keep the catheter within the bladder to drain urine. As further known in the art, the balloon diameter when inflated is larger than the urethral diameter (30F~1 cm) preventing it from slipping out. Unlike other medical devices, urinary catheters are most commonly placed into and removed from patients by nurses, ancillary medical staff, and patients themselves. Physicians and non-physicians alike report not infrequent complications associated with placement (insertion into the patient) and removal of urinary catheters.

Unfortunately, incorrect handling and placement of urinary catheters can result in disastrous consequences. Indeed, urologists are regularly consulted to manage complications associated with misplacement of urinary catheters. The most common complication is the filling of the balloon at the tip of the urinary catheter with water despite it residing within the urethra instead of the bladder. This occurs when the medical staff does not insert the catheter up to the so-called "hub" which the merger of the balloon tube with the drainage tube outside the body. This situation can create significant urethral injury causing the patient great pain and significant bleeding and can necessitate a costly consultation by a surgical specialist. The catheter can usually be replaced after the injury, but may require invasive cystoscopy (e.g., placement of a small camera into the urethra as known in the art). Invariably, in this situation the catheter must remain indwelling for a longer than initially intended period of time to allow the urethra to heal and, in some instances, to provide pressure to halt the bleeding. Other consequences of intra-urethral balloon inflation are urinary tract obstruction, urinary tract infections, discomfort, renal failure, and death. The urethral injury incurred may result in urethral stricture or narrowing (e.g., 7% based upon a single institutional study), which can necessitate additional costly surgical interventions.

Another common complication associated with urinary catheters obtains if the catheter balloon bursts inside of the patient's bladder. This situation can arise for a variety of reasons, including filling by the medical staff in excess of the maximum volume specified by the manufacturer and/or by device malfunction (e.g., defective balloon). In such situations, the catheter "falls out", and requires replacement. More significantly, studies have shown that upon bursting, a fragment of the balloon wall frequently breaks away from the shaft of the catheter and remains within the bladder. The balloon fragment must be retrieved, e.g., with the aid of a cystoscope by a surgical specialist. If the fragment is not removed the patient will have severe urinary symptoms, recurrent urinary tract infections, and over the long-term form stones within the bladder, all of which require further medical intervention and expense.

Moreover, when urethral catheters have a device failure, a common cause is a non-deflating balloon. Current recommendations for managing a non-deflating balloon include percutaneous or endoscopic balloon puncture, instillation of chemicals to dissolve the material comprising the balloon, or over-inflating the balloon to burst it. These techniques, while necessary, can result in balloon fragmentation, patient discomfort, bleeding, and damage to nearby organs.

Moreover, another complication of urinary catheters is the accidental removal of the catheter, while the balloon is still inflated, through the entire length of the urethra. This occurs due to a variety of causes, including catheter tubing snagging on other objects, and in patients with altered mental status who pull out the inflated catheter. This latter event can occur even with a restrained patient or in the presence of a 24-hour attendant. The result is similar to that of inflating the balloon within the urethra, but more severe as it involves the entire urethra. Further complicating premature catheter removal is the necessity to replace the catheter through an already damaged urethra, and possible disruption in some cases of a still healing surgical repair (i.e. after removal of the prostate for cancer or repair of a urethral stricture).

Another common clinical complication associated with indwelling body fluid catheters (e.g., urinary catheters) is that the fluid to be drained can become infected. For example, urinary catheters are known to be not only associated with UTI (urinary tract infection), but the catheter itself is a well-recognized risk factor for the development of a UTI. Indeed, catheter associated UTI (CAUTI) is the foremost common nosocomial (i.e., hospital acquired) infection in the US today, and CAUTI accounts for a significant proportion of health care expenditures, patient morbidity, prolonged hospital stay, and death, in US hospital patients.

In order to prevent infection from arising in and spreading from urinary catheters, a variety of procedures are routinely employed. Catheters must be placed under sterile techniques, and catheter kits with closed drainage systems to help prevent infection are often used. Also, urinary catheter manufacturers typically specify that only sterile water, and never saline, should be used to fill the catheter balloon. Manufacturers also specify that the balloon should generally always be filled with the designed amount (e.g., 10 mL) of sterile water, and not more. However, the scientific rationale for such guidelines is not well described in the literature. Indeed, a recent publication was unsuccessful in conclusively explaining whether use of saline, instead of sterile water, increases the risk of catheter malfunction. See Hui et al., *Int. J. Urol.* 2004, 11:845-847.

The methods and compositions provided herein address these and other problems in the art.

BRIEF SUMMARY OF THE INVENTION

In a first aspect, there is provided a catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet. The catheter further includes a burstable element forming a fluid communication barrier between the second lumen and the first lumen or between the second lumen and space external to the catheter.

In another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet. The catheter further includes a safety balloon in fluid communication with the second lumen, the retention balloon filling inlet and the retention balloon, wherein the safety balloon is disposed distal to the retention balloon filling inlet.

In yet another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet. The catheter further includes a marking on the elongated tubular member, wherein the marking is disposed at a position indicating proper insertion amount for the catheter.

In yet another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a non-fragmenting retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet.

In yet another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and said retention balloon filling inlet. The catheter further includes a slit valve disposed between the first lumen and the second lumen allowing fluid communication between the first lumen and the second lumen upon opening of the slit valve.

In another aspect, there is provided a kit. The kit includes a catheter as disclosed herein and a safety syringe for filling the retention balloon.

BRIEF DESCRIPTION OF THE DRAWINGS

In FIG. 3B, elements 102, and 105-107 are as defined for FIG. 1. As depicted in FIG. 3C, which is a magnified depiction of region 301, a substantially circumferential region 302 of the second arm of the catheter forms the safety balloon. As depicted in FIG. 3D, which is magnified view of element 303 (FIG. 3C), the substantially circumferential region 302 forming the safety balloon can be substantially circumferentially thinned during manufacture, as depicted in the trough (elements 304).

FIG. 4 depicts a safety lock 401 which can positioned over safety balloon 302 (FIG. 3) thereby preventing inflation of the safety balloon.

FIG. 5 depicts a schematic view of a safety catheter described herein, wherein a burstable element (201) is attached to a ripcord 501, and to a more proximal position, e.g., terminating in region 301, giving access to the ripcord external to the body. Pulling the ripcord will burst the burstable element, causing the fluid in the retention balloon and the second lumen to drain into the first lumen, thereby deflating the retention balloon. Other elements defined in FIG. 5 are as defined in FIGS. 1-3.

DETAILED DESCRIPTION OF THE INVENTION

Definitions

Unless expressly defined differently, the terms used herein have their common meanings in the art.

Unless indicated otherwise, the terms "proximal" and "distal" in the context of a catheter refer to positioning relative to outside of a body into which the catheter is inserted. Accordingly, when inserted in a subject, e.g., a human, the proximal end of a catheter is typically outside of the body, and the distal end of the catheter is typically within the body, e.g., within a bladder. The terms "subject" and "patient" are used synonymously herein and refer to a human or non-human mammal, preferably a human.

Figure 1A:
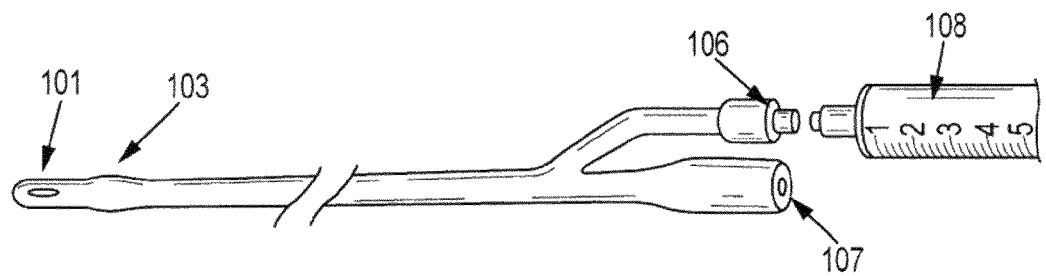
FIG. 1A depicts a urinary catheter. Depicted elements as described herein: fluid inlet (101); retention balloon (103); retention balloon filling inlet (106); fluid outlet (107); and, optional syringe (108) for filling retention balloon.
Figure 1B:
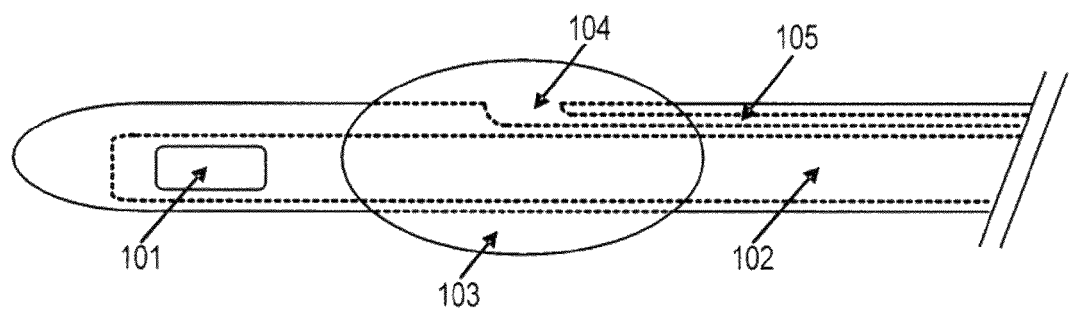
FIG. 1B further depicts a schematic of a catheter. Additional elements of FIG. 1B: fluid tract (e.g., first lumen) (102); balloon filling tract (104); and, fluid tract to fill balloon (e.g., second lumen) (105). The break (i.e., double lines) at the right of the top structure of FIG. 1B indicates continuation with the structure depicted in the bottom of FIG. 1B.
Figure 1B:
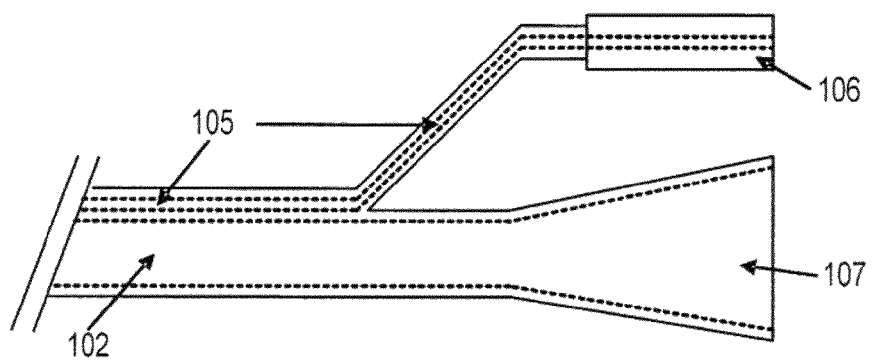

"Catheter" refers in the customary sense to a generally elongated tubular structure inserted into the body to permit introduction or withdrawal of fluids, e.g., liquids and/or air, or to keep a passageway (e.g., urethra) open. Materials for the construction of catheters are well known in the art and include, e.g., latex, silicone, and the like. Catheters are known in many areas of medicine including pulmonology, cardiology, urology, gastroenterology, and the like. The term "safety catheter" refers to a catheter having one or more of the novel features described herein. The terms "conventional catheter" and the like refer, in the customary sense, to catheters known in the art. A urinary catheter is depicted in FIGS. 1A-1B. Elements depicted in FIGS. 1A-1B include: fluid (e.g., urine) inlet (101); fluid (e.g., urine) tract (102), also described as a first lumen in some embodiments herein; inflatable balloon (103), also described as a retention balloon in some embodiments herein; balloon filling tract (104) to fill balloon (103) through fluid (e.g., sterile water) tract (105), also described as a second lumen in some embodiments herein; retention balloon filling inlet (106); and fluid outlet (107). Absent further qualification, the terms "catheter," "safety catheter," "slit valve safety catheter" and the like as used herein refer to devices described herein which employ one or more of the novel elements described herein.

"Elongated tubular member" refers to the generally elongated tubular structure of a catheter. In some embodiments, a catheter is bifurcated at the proximal end (i.e., outside of the body) into a first arm and second arm providing, for example, physical separation of the fluid outlet (107) and retention balloon filling inlet (106). See FIGS. 1A-1B. In some embodiments, the first and/or second arm include additional elements described herein. Further to any embodiment of a catheter described herein, in some embodiments the first arm (i.e., the so-called drainage tube described herein) resulting from the bifurcation at the proximal end of the catheter includes the first lumen as described herein, and the second arm (i.e., the so-called balloon tube described herein) resulting from the bifurcation includes the second lumen. Further to any embodiments of a catheter described herein, in some embodiments the safety balloon is positioned along the length of the second arm.

"Fluid inlet" refers to an opening of a catheter or stent through which bodily fluid can transit through a drainage tube to outside of the body. Conversely, the term "fluid outlet" refers to the end of a drainage tube through which bodily fluid drains.

"First lumen" refers to a fluidic communication (e.g., a closed channel, tube, or the like) between a fluid inlet and a fluid outlet.

"Retention balloon" refers in the customary sense to an inflatable element at the distal aspect of a catheter or stent which when inflated prevents migration of the catheter. For example, in a urinary catheter, inflation of a retention balloon within the bladder prevents migration of the urinary catheter through the urethra and out of the body.

"Retention balloon filling inlet" refers to an inlet (e.g., FIG. 1B, 106) for filling a retention balloon. The retention balloon filling inlet can include a variety of connectors (e.g., locking syringe connectors and the like) to facilitate filling of the retention balloon.

"Second lumen" refers to a fluidic communication (e.g., a channel, tube, or the like) between a retention balloon and a retention balloon filling inlet. In some embodiments, the second lumen is in fluidic communication with a safety balloon as described herein.

"Retention balloon inflation pressure" refers to the pressure required to inflate a retention balloon. Retention balloon inflation pressure can be assessed by methods well known in the art.

"Burstable element" refers to a structural feature forming a fluid communication barrier between lumina such that if the burstable element is burst, then fluid communication between the lumina can commence. In some embodiments described herein, a burstable element is shared by the first and second lumina described herein, and upon bursting of the burstable element, the first and second lumina achieve fluid communication. In some embodiments described herein, a burstable element is disposed in the second lumen wall or in the wall of the retention balloon, and upon bursting of the burstable element, the retention balloon deflates. In some embodiments, the retention balloon deflates by emptying into a space external to the catheter, e.g., directly into the bladder, urethra, or other body cavity. The terms "burst," "rupture" and the like in the context of a retention balloon are synonymous and refer to a physical opening which occurs in the burstable element and which thus provides fluid communication thereby allowing the retention balloon to deflate.

"Burstable element bursting pressure" refers to the pressure required to burst a burstable element. Burstable element bursting pressure can be assessed by methods well known in the art.

"Physically harmful inflation pressure" refers to a pressure sufficient to cause physical harm to a subject, as judged by a reasonably prudent medical practitioner. For example, the ripping and tearing of the urethra which accompanies the forcible removal of a urinary catheter while the retention balloon is inflated results from a physically harmful inflation pressure, and associated physically harmful force, having been applied to the urethra. A physically harmful inflation pressures, in some embodiments, is a pressure at which the retention balloon bursts (e.g. breaks, shatters, rips, etc.). It is understood that pressure refers to force per unit area, and that a force impinged on a burstable element results in a pressure begin applied to the burstable element.

"Pressure-limiting element" refers to a feature in fluid communication with a retention balloon that prevents a defined retention balloon pressure from being exceeded. Exemplary pressure-limiting elements include burstable elements, slit valves, and safety balloons as described herein.

The terms "safety balloon," "circumferential safety balloon," "secondary balloon" and the like refer to an inflatable feature in fluid communication with the second lumen. Accordingly, the safety balloon is in fluid communication with the retention balloon filling inlet and the retention balloon. Thus, a safety balloon is subject to the pressure contained within the second lumen and the retention balloon. In some embodiments disclosed herein, the safety balloon is located distal to the retention balloon filling inlet. In some embodiments, the safety balloon is located on the second arm resulting from a bifurcation of the elongated tubular catheter as described herein.

"Safety balloon inflation pressure" refers to the pressure required to inflate a safety balloon (e.g., partially inflate, fully inflate and in some embodiments inflate sufficiently such that a practitioner can easily observe the inflation relative to non-inflation). Safety balloon inflation pressure can be assessed by methods well known in the art.

The terms "marking" and the like in the context of catheters disclosed herein refer to indicia on, attached to, or movably attached to a catheter, which indicate the proper distance that the catheter should be inserted for a specific subject, e.g., male child, female child, male adult or female adult. The terms "disposed at a position indicating proper insertion amount" and the like refer to the nominal insertion amount for a specific sex and age of subject, as known in the art. In some embodiments, a marking can further indicate an inappropriate insertion amount, e.g., insufficient insertion such that the distal end of the catheter resides within the urethra, prostate, or the like, and does not reside within the bladder.

"Slit valve" refers in the customary sense to an incision in a lumen wall which allows fluid communication across the slit valve only if sufficient pressure is exerted thereon. "Slit valve opening pressure" is the pressure at which a slit valve will open to allow fluid communication. "Slit valve safety catheter" refers to a safety catheter as described herein which employs a slit valve as a pressure-limiting element, rather than or in additional to, a burstable element, safety balloon, or other features described herein.

The terms "non-fragmenting balloon" and the like refer to a balloon (e.g., a retention balloon as described herein) designed to minimize fragmentation; i.e., designed such that when ruptured multiple pieces do not obtain. In some embodiments, a non-fragmenting balloon eliminates fragmentation into multiple pieces upon rupture. Methods for render a balloon non-fragmenting are known in the art and include, e.g., suitable choice of material for construction, encasing at least a portion of the balloon in a compliant yet non-fragmenting covering (e.g., a mesh of nylon and the like), and the like.

"Internally placed catheter" refers to a catheter which resides substantially within the body of a subject. An exemplary internally placed catheter is a stent, as known in the art. Another exemplary internally placed catheter is a catheter which extends from the bladder to a point distal to the prostatic urethra, without terminating outside of the body. In some embodiments, an internally placed catheter includes a string or other mechanical connection which terminates further distally and is available for manipulation by the urologist, for example to deflate a retention balloon and/or remove the internally placed catheter.

Components and Methods for Catheterization

The results from misuse or malfunction of catheters, e.g., urinary catheters, are manifold. In order to quantify the results of misuse or malfunction, an epidemiological analysis was conducted on the incidence of, and an assessment of the impact of, non-infectious urethral catheter related complications for the seven surgical procedures monitored by the Joint Commission and the Centers for Medicare & Medicaid Services as part of the Surgical Care Improvement Project (SCIP). This study is set forth in Example 1 following, which employed a cross-sectional analysis of the 2007 National Inpatient Sample, a 20% stratified sampling of all non-federal U.S. hospitals, using ICD-9 procedure and diagnostic codes to identify inpatient stays for CABG, non-CABG cardiac, hysterectomy, colon, hip, knee, and major vascular surgery experiencing non-infectious urethral catheter related complications. Univariate and multivariate analyses (controlling for patient demographics and emergent versus elective surgery) were used to determine if these complications were associated with greater length of stay (LOS), total hospital costs, and/or death. In summary, 1,420 cases in the US of non-infectious urethral catheter complications occurred in the seven procedures which were analyzed. Patients suffered an incidence of this complication ranging from one in 764 (0.13%, major vascular surgery) to one in 3,089 (0.03%, hysterectomy). If women were excluded, the incidence was highest for colon surgery at a rate of 1 in 551 patients. Univariate analysis found that mean LOS (6 of 7) and total charges (5 of 7) were statistically increased for most procedures after catheter related complications had occurred. Multivariate analysis found significant association between non-infectious urethral catheter related complications and increased mean LOS for five procedure types, but total charges were increased for only one (knee surgery). Mortality rate was not increased for any procedure associated with non-infectious catheter related complication.

In summary, based on the ICD-9 and diagnostic codes, a total of 1,420 cases of NICRC were reported for these 7 procedures. The incidence of NICRC varied by surgical procedure, but was highest for men undergoing colon surgery (0.18% or 1 in 551). Univariate analysis found that mean LOS (6 of 7), UTI (5 of 7), and total charges (5 of 7) were statistically increased for most procedures. Multivariate analysis suggests significant association between NICRC and increased mean LOS and UTI for 5 of 7 procedure types sampled. Total charges were increased for only one (knee surgery). Mortality rate was not increased for any procedure associated with NICRC.

In order to understand the mechanics of catheter function, and in particular the association of such function with urethral injury, the study set forth in Example 2 following was conducted. For example, urethral injury associated with either catheter balloon filling within the urethra, or when a disoriented patient self-removes a full balloon per urethra, can result in very significant immediate and long-term complications (pain, prolonged hospital stay, and recurrent urethral stricture disease). It was hypothesized that the manual force required to either fill a balloon within the urethra or to remove a full balloon per urethra would result in significantly greater balloon pressure, relative to pressures during normal-use. Furthermore, without wishing to be bound by any theory, it was believed that this difference in balloon pressure could be exploited and serves as the basis for the design a novel catheter, aimed at reducing the incidence of such iatrogenic injuries. Accordingly, ex vivo (funnel, "bladder", attached to a 30 French tube, "urethra") and fresh human male cadaver models were used to measure the relative increases in balloon pressure upon filling a 10 cc balloon with sterile water within the urethra, and upon forced removal of a full 10 cc catheter balloon from the bladder. In the ex vivo model, mean (SD) pressures within the 10 cc balloon were on average 3 times higher within the ex vivo "urethra" (177 kPa±34) versus "bladder" (59 kPa±12); in the human cadaver model, mean balloon pressure was 2.2 times higher within the urethra (150 kPa±28) vs. bladder (67 kPa±10). Balloon pressure increased non-linearly during filling within the urethra of both models, resulting in either balloon rupture (silicone catheters) or "ballooning" of the neck of the balloon filling port (latex catheters). Removal of an inflated balloon per the ex vivo model "urethra" and cadaveric urethra, similarly required non-linear increasing force with incrementally greater balloon volumes (e.g. 2.1 lbs±0.1, for 5 cc vs. 9.3 lbs±3.2, for 10 cc balloon volume). In summary, catheter balloon pressures and manual extraction forces during use associated with urethral injury are significantly greater than when associated with normal use. These differences can serve as the basis for new catheters designed to not sustain elevated balloon pressures or extraction forces associated with urethral injury. See Example 2.

As set forth in Example 2, the pressure exerted on the inflated retention balloon during self removal or during snagging of the catheter tubing when the balloon is pulled through the urethra is significantly higher than the pressure exerted on it within the urinary bladder. Accordingly, it was conceived that the retention balloon can have material or geometric properties designed to mitigate this increased pressure and cause the retention balloon to rupture at a predetermined pressure prior to the result of physical harm to the subject. For example, the back half or most distal portion of the balloon could be thicker than the front half. Thus, when a patient accidentally removes the inflated catheter the pressure in the most proximal portion of the balloon rises and causes the balloon to rupture resulting in rapid deflation thereby preventing patient injury. This concept arose from pulling an inflated catheter through a funnel which we used as our model of the bladder becoming the urethra. See Example 2. We noted that the balloon of an inflated catheter takes on a significantly altered shape that causes the proximal portion of the balloon to bulge profoundly. Yet another design feature of the retention balloon to allow large pressures to be mitigated involves a burstable element, as defined herein, which can preferentially burst at a defined pressure, thus allowing deflation of the retention balloon before physical harm ensues.

Accordingly, in a first aspect, there is provided a catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet. The catheter further includes a burstable element forming a fluid communication barrier between the second lumen and the first lumen or between the second lumen and space external to the catheter.

Further to any embodiment disclosed herein, where the fluid inlet is "disposed at the distal end" it is understood that the fluid inlet may be at the distal end of the catheter, or near the distal end of the catheter. In some embodiments, the fluid inlet is 0-20, 0-10, 0-8, 0-6, 0-4, or even 0-2 cm from the distal end of the catheter. In some embodiments, the fluid inlet is 0, 1, 2, 3, 4, 5, 6, 7, 8, 9, 10, 11, 12, 13, 14, 15, 16, 17, 18, 19, 20 cm or even more removed from the distal end of the catheter.

Further to any embodiment disclosed herein, where the retention balloon is "disposed at the distal end" it is understood that the retention balloon may be at the distal end of the catheter, or near the distal end of the catheter. In some embodiments, the retention balloon is 0-20, 0-10, 0-8, 0-6, 0-4, or even 0-2 cm from the distal end of the catheter. In some embodiments, the fluid inlet is 0, 1, 2, 3, 4, 5, 6, 7, 8, 9, 10, 11, 12, 13, 14, 15, 16, 17, 18, 19, 20 cm or even more removed from the distal end of the catheter. In some embodiments, the retention balloon is distal with respect to the fluid inlet. In some embodiments, the fluid inlet is distal with respect to the retention balloon.

Further to any embodiment disclosed herein, where the fluid outlet is "disposed at the proximal end" it is understood that the fluid outlet is at or near the proximal end of the catheter. In some embodiments, the fluid outlet forms the proximal end of the catheter. In some embodiments, the fluid outlet forms the end of one of the arms formed by a bifurcation of the catheter as described herein. In some embodiments, the fluid outlet is 0-20, 0-10, 0-8, 0-6, 0-4 or 0-2 cm from the end of the catheter or bifurcated arm thereof.

Further to any embodiment disclosed herein, where the retention balloon filling inlet is "disposed at the proximal end" it is understood that the retention balloon filling inlet is at or near the proximal end of the catheter. In some embodiments, the retention balloon filling inlet forms the proximal end of the catheter or bifurcated arm thereof as described herein. In some embodiments, the retention balloon filling inlet is 0-20, 0-10, 0-8, 0-6, 0-4 or 0-2 cm from the proximal end of the catheter or bifurcated arm thereof.

Figure 2:
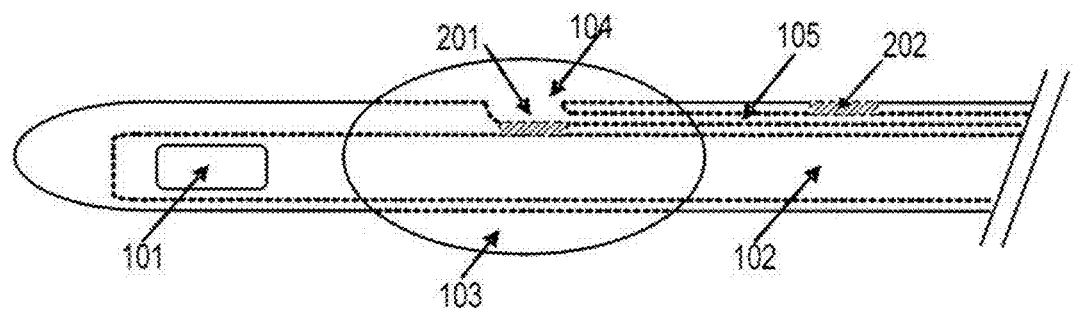
FIG. 2 depicts a catheter as described herein incorporating a burstable element. Exemplary burstable element 201 can form a fluid communication barrier between the first and second lumina. Exemplary burstable element 202 can form a fluid communication barrier between the second lumen and space external to the catheter. Elements 101-105 are as described for FIGS. 1A-1B.

In some embodiments, the burstable element forming a fluid communication barrier between the second lumen and the first lumen or between the second lumen and space external to the catheter, is incorporated into a wall forming either the first lumen or the second lumen. As depicted in FIG. 2, burstable elements can be positioned in a variety of positions. For example, exemplary burstable element 201 (FIG. 2) can form a fluid communication barrier between the first and second lumina. Exemplary burstable element 202 can form a fluid communication barrier between the second lumen and space external to the catheter. In some embodiments, a burstable element has a length of 0-20, 0-10, 0-8, 0-6, 0-4 or 0-2 cm. In some embodiments, a burstable element is 0.1, 0.2, 0.3, 0.4, 0.5, 0.6, 0.7, 0.8, 0.9, 1.0, 1.2, 1.4, 1.6, 1.8, 2.0 cm or even greater in length. In some embodiments, a burstable element has a width of 0-10, 0-8, 0-6, 0-4, or 0-2 cm. In some embodiments, a burstable element is 0.1, 0.2, 0.3, 0.4, 0.5, 0.6, 0.7, 0.8, 0.9, 1.0, 1.2, 1.4, 1.6, 1.8, 2.0 cm or even greater in width.

In some embodiments of this aspect, the catheter further includes one or more additional features described herein. In some embodiments, the catheter includes or further includes a safety balloon, as described herein, in fluid communication with the second lumen, the retention balloon filling inlet and the retention balloon, wherein the safety balloon is disposed distal to the retention balloon filling inlet.

In some embodiments, the catheter includes or further includes a marking, the marking disposed at a position indicating proper insertion amount for the catheter. In some embodiments, the marking indicates the proper amount of insertion for a specific subject, e.g., male child, female child, male adult, or female adult. In some embodiments, the marking indicates that the catheter has been inserted less than the proper amount. In some embodiments, a plurality of markings are provided for different patient types, such as male, female, adult, child, etc.

Further to any embodiment disclosed herein, the marking may be permanently affixed to the catheter, e.g., affixed, printed or otherwise applied during or after manufacture of the catheter. Further to any embodiment incorporating a marking for proper insertion amount disclosed herein, the marking may be movably affixed to the catheter, e.g., a circumferential indicator (e.g., a movable tag) and the like. Further to any embodiment disclosed herein, the marking may be a plurality of markings, each indicating the proper insertion amount for a specific type of subject, e.g., male child, female child, male adult, or female adult. Further to any embodiment disclosed herein, the marking may be a plurality of markings, at least one of which indicates the proper insertion amount for a specific type of subject, e.g., male child, female child, male adult, or female adult, and at least one of which indicates that less than the proper amount of insertion has been achieved during insertion.

In some embodiments, the catheter includes or further includes a slit valve disposed between the first lumen and the second lumen allowing fluid communication between the first lumen and the second lumen upon opening of the slit valve.

In some embodiments, the catheter includes or further includes a retention balloon which is a non-fragmenting balloon as described herein.

Yet further to this aspect, in some embodiments the burstable element bursts at a burstable element bursting pressure, wherein the burstable element bursting pressure is less than a physically harmful inflation pressure. In some embodiments, the burstable element is not burst and the second lumen is not in fluid communication with the first lumen or space external to the catheter. In some embodiments, the burstable element is burst and the second lumen is in fluid communication with the first lumen or the space external to the catheter.

In another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet. The catheter further includes a safety balloon in fluid communication with the second lumen, the retention balloon filling inlet and the retention balloon, wherein the safety balloon is disposed distal to the retention balloon filling inlet.

In some embodiments of this aspect, the catheter further includes one or more additional features described herein. In some embodiments, the catheter includes or further includes a burstable element, as described herein, forming a fluid communication barrier between the second lumen and the first lumen or between the second lumen and space external to the catheter.

In some embodiments, the catheter includes or further includes a marking, as described herein, the marking disposed at a position indicating proper insertion amount for the catheter.

In some embodiments, the catheter includes or further includes a slit valve, as described herein, disposed between the first lumen and the second lumen and allowing fluid communication between the first lumen and the second lumen upon opening of the slit valve. In some embodiments, the slit valve opens at a slit valve opening pressure. In some embodiments, the slit valve opening pressure is less than a physically harmful inflation pressure.

In some embodiments, the catheter includes or further includes a retention balloon which is a non-fragmenting balloon as described herein.

Further to this aspect or embodiments thereof, in some embodiments the retention balloon inflates at a retention balloon inflation pressure, the safety balloon inflates at a safety balloon inflation pressure, and the safety balloon inflation pressure is greater than the retention balloon inflation pressure. In some embodiments, the safety balloon inflation pressure is less than a physically harmful inflation pressure.

Further to any aspect or embodiment described herein incorporating a safety balloon, in some embodiments the safety balloon inflates, in response to excessive pressure within the retention balloon or second lumen, to provide a warning indication and to provide relief of pressure. The terms "provide relief of pressure" and the like in this context refer to inflation of the safety balloon thereby mitigating excessive pressure in the retention balloon or second lumen. Excessive pressure within the retention balloon or second lumen is mitigated until the safety balloon reaches a maximum inflation size. The terms "warning indication" and the like mean an indication that a problem exists in the placement or usage of the catheter, e.g., excessive pressure in the retention balloon or second lumen. Thus, a warning indication provides an alert to the subject of catheterization or medical personnel of a problem involving excessive pressure within the retention balloon or second lumen. The warning indication can take a variety of forms. In some embodiments, inflation (i.e., change in size and/or shape) of the safety balloon is a warning indication. In some embodiments, inflation of the safety balloon is accompanied by a change in color of the safety balloon, e.g., red, yellow and the like, to make the warning indication readily apparent.

Further to any aspect or embodiment described herein incorporating a safety balloon, in some embodiments the safety balloon is circumferential. The term "circumferential" in this context means that the safety balloon includes a region of the catheter or arm thereof which extends around the entire circumference of the catheter or arm thereof. Accordingly, the term "safety balloon is circumferential" means that the safety balloon includes a region of the catheter or arm thereof which extends around the entire circumference of the catheter or arm thereof. In some embodiments, the safety balloon is substantially circumferential upon inflation. The term "safety balloon is substantially circumferential" means that the safety balloon includes a region of the catheter or arm thereof which substantially extends around the circumference of the catheter or arm thereof, e.g., 50%, 55%, 60%, 65%, 70%, 75%, 80%, 85%, 90%, 95% or even greater around the circumference of the catheter or arm thereof. In some embodiments, the safety balloon inflates to a substantially spherical shape. In some embodiments, the safety balloon inflates to a substantially ellipsoidal shape, e.g., in the case of less than complete inflation to a substantially spherical shape. It is understood that a substantially circumferential safety balloon or circumferential safety balloon is not a focal safety balloon. The term "focal safety balloon" refers to a safety balloon which merely extends around part of the circumference of the catheter or arm thereof, e.g., <50%, <40%, <30%, <20%, <10% or even less.

Further to any aspect or embodiment described herein incorporating a safety balloon, in some embodiments, the region of the catheter which will function as the safety balloon upon inflation is circumferentially scored, thinned, or otherwise fabricated such that upon inflation the safety balloon is circumferential. The terms "circumferentially scored, thinned or otherwise fabricated" and the like in this context refer to a feature, e.g., a scoring or thinning, which extends about the entire circumference of another feature, e.g., the circumference of a catheter or arm thereof. In some embodiments, the region of the catheter which will function as the safety balloon upon inflation is substantially circumferentially scored, thinned, or otherwise fabricated such that upon inflation the safety balloon is substantially circumferential. In some embodiments, the region of the catheter which will function as the safety balloon upon inflation is substantially circumferentially scored, thinned, or otherwise fabricated such that upon inflation the safety balloon is substantially spherical in shape. The terms "substantially circumferentially scored, thinned or otherwise fabricated" and the like in this context refer to a feature, e.g., a scoring or thinning, which substantially extends about the circumference of another feature, e.g., the circumference of a catheter or arm thereof. In some embodiments, the region of the catheter or arm thereof (e.g., second arm as described herein) which will function as the inflated safety balloon is scored, thinned, or otherwise fabricated to encompass less than the entire circumference of the catheter or arm thereof. In some embodiments, the less than the entire circumference of the catheter or arm thereof is about 10%, 15%, 20%, 25%, 30%, 35%, 40%, 45%, 50%, 55%, 60%, 65%, 70%, 75%, 80%, 85%, 90%, 92%, 94%, 96%, 98%, or even 99% of the circumference of the catheter or arm thereof. In some embodiments, the inflated safety balloon is scored, thinned, or otherwise fabricated to encompass about 50% of the circumference of the catheter or arm thereof, and the resulting inflated safety balloon is substantially hemispherical in shape. Absent express indication otherwise, the term "about" in the context of a numeric value means the nominal value ±10% thereof.

It is understood that the safety balloon can reversibly inflate and deflate during usage. Accordingly, in the event of a warning indication, steps can be taken to mitigate excessive pressure and thereby continue using the same catheter without the need to replace the catheter. Exemplary steps to mitigate excessive pressure can include deflation of the retention balloon, repositioning of the catheter, e.g., further insertion to position the retention balloon fully within the bladder, and reinflation of the retention balloon without the need to replace the catheter.

Figure 3A:
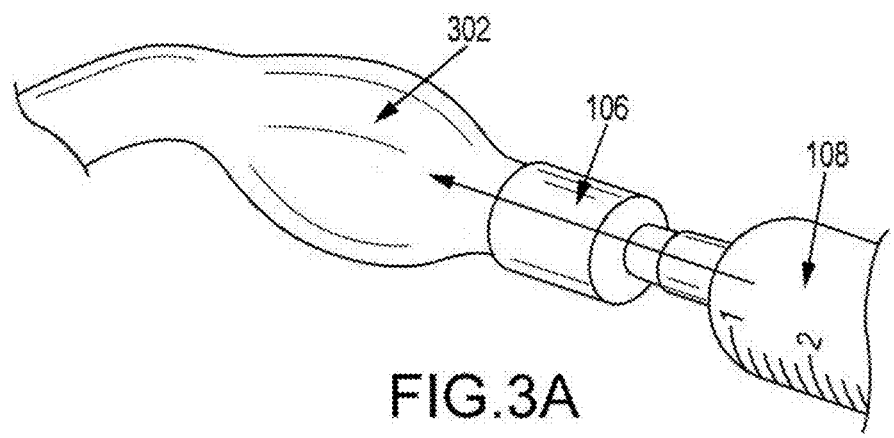
FIG. 3A depicts a perspective view of the second arm of a bifurcated elongated tubular member (i.e., arm of a catheter for filling retention balloon) as described herein. Element 302 depicts a partially full safety balloon. Other elements are as defined in FIG. 1.
Figure 3B:
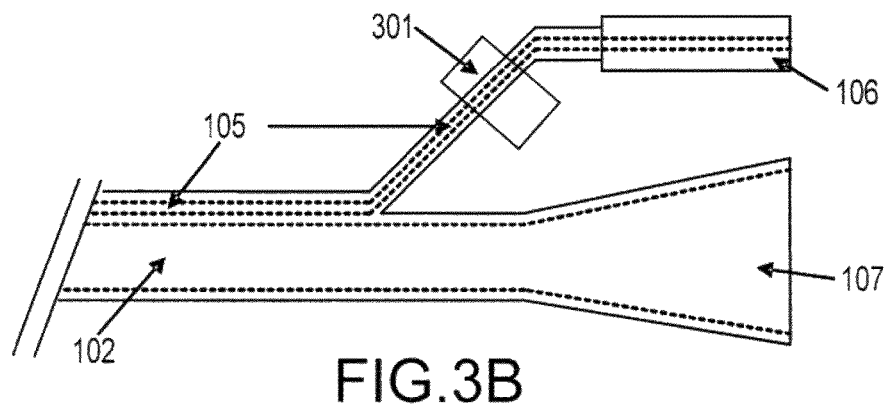
FIG. 3B depict an exemplary safety balloon (uninflated) positioned within boxed region 301.
Figure 3C:
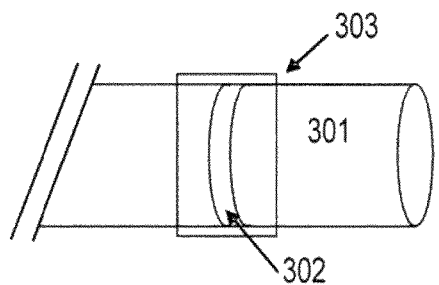
FIG. 3E depicts a perspective view of a partially inflated safety balloon 302. Elements 102 and 106 and 108 are as defined in FIG. 1.

Further to any aspect or embodiment described herein incorporating a safety balloon, FIG. 3A depicts an exemplary second arm of a catheter, as defined herein, with a partially filled safety balloon 302. As depicted in schematic FIG. 3B, an exemplary safety balloon (uninflated) can be positioned within boxed region 301. As depicted in FIG. 3C, which is a magnified depiction of region 301, a substantially circumferential region 302 of the second arm of the catheter can be thinned, scored, or otherwise fabricated to preferentially inflate (i.e., with respect to the adjoining material forming the catheter or second arm thereof), thereby providing a controlled shape to the safety balloon upon inflation, e.g., the safety balloon can be substantially spherical, hemispherical, ellipsoidal or the like, upon inflation.

Figure 3D:
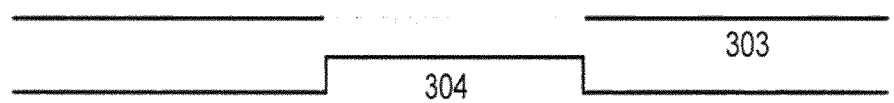
Figure 3D:
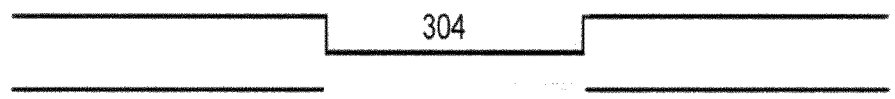

Further to any aspect or embodiment described herein incorporating a safety balloon, in some embodiments, as depicted in FIG. 3D, the substantially circumferential region 302 forming the safety balloon is substantially circumferentially thinned during manufacture, e.g., by formation of a trough (elements 304 of FIG. 3D). In some embodiments, the trough is internal, representing a widening of the second lumen in the region which will form the expanded safety balloon. In some embodiments, the trough forms part of the external aspect of the catheter or second arm thereof, forming a narrower region of the outside of the elongated tubular member, e.g., second arm as described herein, which when inflated will form the safety balloon.

Further to any aspect or embodiment described herein incorporating a safety balloon, in some embodiments, the substantially circumferential region 302 is colored differently than the adjoining material of the catheter, e.g., material forming the second arm. In some embodiments, the safety balloon changes color upon inflation. Such color change can result, for example, from a thinning (e.g., stretching) of the material forming the safety balloon during inflation, or the exposure of an underlying color not externally observed when the safety balloon is deflated, and the like. For example, the outer aspect, i.e., outer coat, of the safety balloon can be painted with a distinctive color (e.g., green) and have an undercoat of another color (e.g., red). The outer coat can be applied, e.g., as a paint, during or after manufacture, or the outer coat can be included during manufacture by appropriate choice of colored material to form the safety balloon. The undercoat may be applied, e.g., as a paint, prior to manufacture or painting of the outer coat, the undercoat may be painted on the inner aspect of the safety balloon, or the undercoat may form part of the material forming the inner aspect of the safety balloon. In some embodiments, the outer coat includes a material, e.g., paint, which is less elastic than the material forming the safety balloon and/or the material forming the undercoat. In some embodiments, the outer coat includes a material which is thinner than the material forming the safety balloon and/or the material forming the undercoat. Accordingly, upon inflation of the safety balloon, the color of the outer coat diminishes in intensity due to the stretching of the safety balloon and outer coat, and the color of the undercoat appears due to greater elasticity and/or thickness of the undercoat relative to the outer coat. In some embodiments, the outer coat is green, the undercoat is red, and the green color disappears and is replaced by red during inflation of the safety balloon. In some embodiments, a different set of contrasting colors is employed in the outer coat and undercoat. In some embodiments, the outer coat in the uninflated safety balloon is effectively the same color as the material adjoining the safety balloon, and the color of the undercoat does not appear until inflation of the safety balloon.

In some embodiments, substantially circumferential region 302 is bounded proximally and/or distally by thin colored lines (e.g., green lines or the like). Upon inflation of the safety balloon, the thin colored lines effectively disappear as the material forming the safety balloon stretches. Accordingly, disappearance of the thin colored lines and/or appearance of the inflated safety balloon can signal a warning indication as described herein.

Further to any aspect or embodiment described herein which includes a safety balloon, in some embodiments the region of the elongated tubular member in which the uninflated safety balloon is positioned has substantially the same diameter as the adjoining regions of the elongated tubular member which do not include the uninflated safety balloon. In some embodiments where the safety balloon resides in the second arm formed by bifurcation of the elongated tubular member as described herein, the region of the second arm which includes the uninflated safety balloon has substantially the same diameter as the adjoining regions of the second arm which do not include the uninflated safety balloon. In some embodiments, the diameter of the uninflated safety balloon is less than the diameter of the adjoining regions of the second arm. In some embodiments, the diameter of the uninflated safety balloon is greater than the diameter of the adjoining regions of the second arm.

Figure 3E:
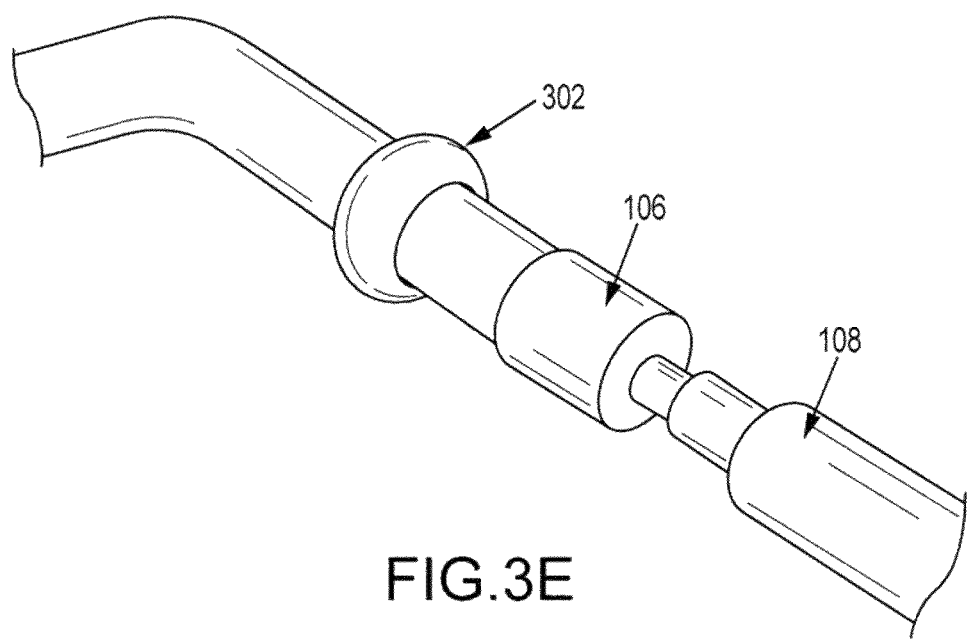

A perspective view of an inflated safety balloon 302 is depicted in FIG. 3E. In some embodiments, the safety balloon is colored (i.e., red, yellow, or the like, indicated by a darkening of the region in the figure) to indicate a warning when inflated.

Further to any aspect or embodiment described herein incorporating a safety balloon, in some embodiments there is additionally included a safety balloon lock out permitting selective inflation of the safety balloon. An exemplary safety balloon lock out is depicted in FIG. 4, element 401, which in some embodiments can be adjusted by sliding to either cover the uninflated safety balloon, thereby disabling the safety balloon, or to uncover the safety balloon, thereby enabling its use. Thus, in some embodiments, a lock out mechanism is included that allows the safety balloon to be active, for example, only during catheter insertion. Once the catheter is appropriately placed within the bladder and inflated, the lock out mechanism is activated to disable the safety balloon from expanding, thereby preventing migration (e.g., removal) of the catheter. This lock-out mechanism eliminates the potential usefulness of deflation of the retention balloon to the patient who might be at risk for ripping out his/her catheter accidentally. In some embodiments, this lock-out mechanism is an outer tube of plastic or some other non-elastic material which can be moved to surround the safety balloon. When in the open position the lock out mechanism allows for the safety balloon to be inflated, for example during catheter insertion. Then, the lock out mechanism can be rotated or slid into a different (e.g., closed) position overlying the safety balloon thereby disallowing it from being inflated once the retention balloon is safely inflated within the bladder. In some embodiments, the lock out mechanism further includes a locking mechanism to keep it in the locked position.

In another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet. The catheter further includes a marking, as described herein, wherein the marking is disposed at a position indicating proper insertion amount for the catheter.

In some embodiments of this aspect, the catheter further includes one or more additional features described herein. In some embodiments, the catheter includes or further includes a burstable element, as described herein, forming a fluid communication barrier between the second lumen and the first lumen or between the second lumen and space external to the catheter.

In some embodiments, the catheter includes or further includes a safety balloon, as described herein, in fluid communication with the second lumen, the retention balloon filling inlet and the retention balloon, wherein the safety balloon is disposed distal to the retention balloon filling inlet.

In some embodiments, the catheter includes or further includes a slit valve, as described herein, disposed between the first lumen and the second lumen allowing fluid communication between the first lumen and the second lumen upon opening of the slit valve.

In some embodiments, the catheter includes or further includes a retention balloon which is a non-fragmenting balloon as described herein.

In some embodiments, the marking is disposed at a position indicating proper insertion amount for the catheter for a male. In some embodiments, the marking is disposed at a position indicating proper insertion amount for the catheter for a female. In some embodiments, the marking is disposed at a position indicating proper insertion amount for the catheter for a child. In some embodiments, the marking is disposed at a position indicating proper insertion amount for the catheter for a male child. In some embodiments, the marking is disposed at a position indicating proper insertion amount for the catheter for a female child.

In another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a non-fragmenting retention balloon disposed at the distal end. The catheter further includes a retention balloon filling inlet disposed at the proximal end. The catheter further includes a second lumen within the elongated tubular member providing fluidic communication between the retention balloon and the retention balloon filling inlet.

In some embodiments of this aspect, the catheter further includes one or more additional features described herein. In some embodiments, the catheter includes or further includes a burstable element, as described herein, forming a fluid communication barrier between the second lumen and the first lumen or between the second lumen and space external to the catheter.

In some embodiments, the catheter includes or further includes a safety balloon, as described herein, in fluid communication with the second lumen, the retention balloon filling inlet and the retention balloon, wherein the safety balloon is disposed distal to the retention balloon filling inlet.

In some embodiments, the catheter includes or further includes a marking, as described herein, the marking disposed at a position indicating proper insertion amount for the catheter.

In some embodiments, the catheter includes or further includes a slit valve, as described herein, disposed between the first lumen and the second lumen allowing fluid communication between the first lumen and the second lumen upon opening of the slit valve.

Further to any embodiment described herein, in some embodiments the non-fragmenting retention balloon is fabricated from a non-fragmenting elastic material. Non-fragmenting elastic materials suitable for use in such embodiments are known in the art. In some embodiments, the non-fragmenting retention balloon is at least partially encased in a safety mesh, as described herein.

In yet another aspect, there is provided another catheter. The catheter includes an elongated tubular member which includes a proximal end and a distal end. The catheter further includes a fluid inlet disposed at the distal end in fluid communication with a fluid outlet disposed at the proximal end. The catheter further includes a first lumen within the elongated tubular member providing fluidic communication between the fluid inlet and the fluid outlet. The catheter further includes a retention balloon disposed at the distal end. The catheter further includes a retention balloon filling inlet disposed at the proximal end. The catheter further includes a second lumen within the elongated tubular member providing fluidic communication between the retention balloon and said retention balloon filling inlet. The catheter further includes a slit valve, as described herein, disposed between the first lumen and the second lumen allowing fluid communication between the first lumen and the second lumen upon opening of the slit valve. In some embodiments, the slit valve is disposed in the second lumen allowing fluid communication between the second lumen and space external to the catheter upon opening of the slit valve. In some embodiments, the slit valve resides on the second arm as described herein.

In some embodiments of this aspect, the catheter further includes one or more additional features described herein. In some embodiments, the catheter includes or further includes a burstable element, as described herein, forming a fluid communication barrier between the second lumen and the first lumen or between the second lumen and space external to the catheter.

In some embodiments, the catheter includes or further includes a safety balloon, as described herein, in fluid communication with the second lumen, the retention balloon filling inlet and the retention balloon, wherein the safety balloon is disposed distal to the retention balloon filling inlet.

In some embodiments, the catheter includes or further includes a marking, as described herein, on the elongated tubular member, the marking disposed at a position indicating proper insertion amount for the catheter.

In some embodiments, the catheter includes or further includes a retention balloon which is a non-fragmenting balloon as described herein.

Physiochemical Properties of Catheters

Without wishing to be bound by any theory, it is believed that the enclosing wall of a conventional catheter "balloon membrane" (i.e. the material that comprises the inflatable balloon portion of the catheter) may not be completely impermeable, but only semi-permeable. For example, Studer et al. (*Urology*, Sep. 1983) showed that silicone catheter balloons, tested in-vitro, do in fact leak fluid out, across the balloon wall, to the environment. They further showed that when the balloon was filled with 5 mL of sterile water and maintained in human urine at 22° C. (*body temperature is 37° C.), 34% of the sterile water in the balloon is lost over 4 weeks. When the balloon is filled with 5 mL of saline (0.9% NaCl), only 40% of the 5 mL remains within the balloon after 4 weeks.

Thus, if the balloon is only semi permeable, and, bacteria and other electrolytes and proteins can traverse the balloon membrane, then, this could explain several clinically important observations. First, the balloon portion of a catheter sometimes cannot be deflated, suggesting obstruction of some portion of the balloon channel. We hypothesize that if bacteria do enter the balloon lumen or balloon filling-port channel, then, once in place, bacteria could create "biofilm" (a normal by-product of bacteria exposed to an indwelling prosthetic device, such as a catheter), and, cause obstruction. Second, if bacteria can penetrate the lumen of the catheter balloon, it is possible (and indeed likely) that bacteria can elaborate biofilm within this space, and thereby remain "protected" from the body's natural defenses, and/or any antibiotics administered to the patient and present within blood or urine. Thus, bacterial translocation across the catheter balloon wall could, in this way, lead to CAUTI that is refractory to antibiotic administration, and/or UTI persistence (which could be mistaken for UTI "recurrence").

Moreover, if water does pass through a catheter balloon, then an additional consequence is that the balloon will deflate over time (as described by Studer et al. Id.), and, as a consequence of this, could lead to the catheter "falling out" from the patient, and/or, migrating distally to the prostatic urethra, where the drainage inlet could become obstructed and result in outflow obstruction and attendant morbidity. It is noteworthy in this context that Studer et al. (Id.), despite the small sample sizes in their in-vitro study (5 catheters filled with one of 5 different solutions of increasing osmolality), did not report "encrustation" or an inability to deflate the catheter balloon after 4 weeks with, in some cases, highly osmotic/salt-containing fluid. Furthermore, their study was performed in vitro, using sterile human urine to bathe the catheter balloons. It is possible, and consistent with our hypothesis, that bacteria within the urine/bladder are necessary to create balloon malfunction, wherein the bacteria translocate into the balloon/balloon filling port lumen and create biofilm which obstructs the balloon port lumen and prevents the catheter from being decompressed after an extended period of time. Moreover, catheter balloon malfunction could also be explained independent of bacteria if over time water or other ions from the solution that filled the balloon are lost, whereby the concentration of the remaining ions in solution within the balloon increase, and crystallization ensues.

Accordingly, further to any catheter described herein, in some embodiments there is provided a catheter retention balloon fitted with an outer layer of material that is impermeable to water, bacteria, and mineral ions. This outer material coat may include a layer (e.g., single layer or multiple layers) of material that resides in a "pleated" configuration before the catheter is placed in a subject. The pleats allow the outer covering to radially accommodate a silicone, latex (or other standard balloon material) balloon during filling. Before the balloon is ever filled, the pleated "flat" configuration of the balloon facilitates easy delivery via the urethra into the bladder lumen. In some embodiments, the retention balloon outer layer described above can be made of any of a number of modern synthetic materials, known in the art, which are impermeable to water, bacteria, or electrolytes, such as Teflon™, single or multi-ply Latex, or, other plastics or non-plastic materials. In some embodiments, the impermeable reinforcing layer of material, as described herein, is located in the interior of retention balloon lumen, as opposed to the outside of the retention balloon, as described above. Inside, the reinforcing layer can also assume a "pleated" configuration. A variety of pleated configurations are possible, with all having the same goal to minimize the space occupied by the impermeable layer when the balloon is not yet filled with fluid.

In some embodiments, the retention balloon assumes a shape upon inflation other than a spherical shape. Exemplary shapes in this context include portions of a sphere, e.g., a hemispherical shape. Further exemplary shapes include two to four arms oriented perpendicularly to one another and to the long axis of the catheter. These, when filled, secure the catheter inlet end at the bladder neck, while preventing the bladder neck, or bladder wall, from collapsing over the catheter inlet to obstruct it. In some embodiments, an alternative balloon design is employed having a "ring" shape, similar to an automobile wheel "inner tube", that, when filled, surrounds the catheter (balloon-end) circumferentially, thereby preventing the long narrow shaft of the catheter from becoming buried in the bladder wall or bladder neck. In some embodiments, to specifically prevent bacterial colonization of the balloon or catheter inner lumen(s), the interior of the catheter is coated with any of the numerous proprietary "silver coatings", or other bacterio-static and/or bacteriocidal chemical coatings. In such a case, it may not be necessary to modify existing catheter balloon designs at all, or, at least, significantly so. In some embodiments, the retention balloon lumen contains a powdered form of an antibiotic, to maintain bacteriocidal or bacterio-static activity upon dissolution with saline or sterile water.

Accordingly, further to any embodiment of a safety catheter described herein, in some embodiments, the retention balloon is fabricated with an outer layer of material that is impermeable to water, bacteria, and mineral ions. This outer material coat can consist of a single layer of material that resides in a "pleated" configuration before the catheter is ever used. The pleats allow the outer covering to radially accommodate a silicone, latex (or other standard balloon material) balloon during filling. Before the balloon is ever filled, the pleated "flat" configuration of the balloon facilitates easy delivery via the urethra into the bladder lumen.

In some embodiments, the retention balloon is adapted to be impermeable to water, bacteria and mineral ions. In some embodiments, the retention balloon is adapted to be impermeable to water. In some embodiments, the retention balloon is adapted to resist fragmentation in the event of rupture, as described herein.

Further Safety Embodiments

Without wishing to be bound by any theory, it is believed that the current method of notifying medical personnel to the size of the inflatable balloon for a particular catheter is archaic and incomplete. For example, many standard catheters disclose "5 cc" on the balloon port despite company recommendations to fill the balloon with 10 cc. Indeed, the same is commonly observed for larger balloons, e.g., a 30 cc balloon is recommend to receive 35 cc. Additionally, the appropriate fluid to be instilled is sterile water, according to manufacture guidelines and medical literature. Alternative fluids, such as normal saline, which is frequently used by unknowing medical personnel to inflate catheter balloons, may result in balloon crystallization and a non-deflatable balloon. Accordingly, in certain embodiments of any of the catheters disclosed herein, the catheter is labeled with appropriate indicia (i.e., "filling indicia") to state the correct amount and type of fluid that should be instilled into the catheter balloon. In some embodiments, the labeling is printed on the catheter. In some embodiments, the labeling is affixed to the catheter. In some embodiments, the catheter is labeled with appropriate indicia on the first arm as described herein. In some embodiments, the catheter is labeled with appropriate indicia on the second arm as described herein.

It is further believed that force, e.g., pulling tension, can be useful to burst and rapidly deflate an inflated retention balloon, or a lumen in fluidic communication with a retention balloon, thereby preventing patient harm from accidental removal of an inflated catheter. It was discovered during funnel experiments (see Example 2) that an extreme amount of force was required to rip an inflated balloon through a funnel. We propose that a material with tensile strength characteristics different (e.g., weaker) from that from which a catheter is made can be used in order to cause the retention balloon itself, or anywhere along the connecting lumen, to rupture when a certain force is reached.

Accordingly, further to any catheter described herein, in some embodiments there is further provided a first ripcord. The first ripcord includes a first substantially non-elastic cord body, a distal end attached to the burstable element of the safety catheter and adapted to cause bursting of the burstable element upon application of a force sufficient to exceed the burstable element bursting pressure, and a proximal end disposed at the proximal end of the elongated tubular member. In some embodiments, the first substantially non-elastic cord body is substantially disposed within the second lumen. In some embodiments, the first substantially non-elastic cord body is substantially disposed within the first lumen. An exemplary safety catheter employing a first ripcord is depicted in FIG. 5 which depicts a schematic view of a safety catheter described herein, wherein a burstable element (201) is attached to a ripcord 501, and to a more proximal position, e.g., within region 301, giving access to the ripcord external to the body. Pulling the ripcord will burst the burstable element, causing the fluid in the retention balloon and the second lumen to drain into the first lumen, thereby deflating the retention balloon. In some embodiments, the first ripcord extends to the proximal end of the safety catheter substantially through the first lumen. In some embodiments, the first ripcord extends to the proximal end of the safety catheter substantially through the second lumen. In some embodiments, the ripcord is attached to burstable element 202 (FIG. 5) such that when the ripcord is pulled, burstable element 202 bursts, and the contents of the second lumen empty into space external to the catheter.

In some embodiments, the first ripcord extends through the second lumen to the safety balloon or even more proximal, whereby the first ripcord is available to a practitioner when the safety balloon is cut open. In some embodiments, the first ripcord can be accessed by opening (e.g., cutting) the safety balloon.

Further to any catheter described herein, in some embodiments there is provided a second ripcord, which second ripcord includes a second substantially non-elastic cord body, a distal end attached to the burstable element and adapted to cause bursting of the burstable element upon application of a force sufficient to exceed the burstable element bursting pressure, and a proximate end disposed within either the first lumen wall or the second lumen wall. In some embodiments, the second substantially non-elastic cord body is substantially disposed within the first lumen wall or the second lumen wall. In some embodiments, the second substantially non-elastic cord body is disposed substantially within the first lumen wall. In some embodiments, the second substantially non-elastic cord body is disposed substantially within the second lumen wall. In some embodiments, a portion of the second ripcord extends toward the proximal end of the safety catheter substantially through the first lumen. In some embodiments, a portion of the second ripcord extends toward the proximate end of the safety catheter substantially through the second lumen. In some embodiments, the second ripcord causes bursting of the burstable element when the safety catheter is withdrawn while the retention balloon is inflated.

Further to any aspect or embodiment described herein, additional embodiments are contemplated to limit the pressure within the retention balloon and subsequent physical harm such pressure can cause, including the following: a) an outer sheath that attaches to the retention balloon and causes it to rupture when a certain force is reached; b) lining of the entire balloon port (i.e., retention balloon and lumen) or retention balloon with a less elastic material which breaks the wall between the outflow and balloon port at a certain force; c) a slit valve between retention balloon and outflow port that would stretch open when a certain amount of force opens it; and d) a weakness in the most distal portion of the catheter that would tear off when accidentally pulled on so that the retention balloon would deflate and the catheter would fall out.

In some embodiments, a weave, ribbing of filaments, or other tether within the retention balloon material (e.g., balloon wall) is contemplated that prevents disassociation of the retention balloon wall from the catheter in the event of rupture, thereby allowing a ruptured retention balloon to be removed with the catheter as one unit in the event that the balloon was accidentally or purposefully ruptured. This feature is useful to eliminate the need for costly surgical procedures to remove balloon fragments.

In some embodiments, a strip of material is embedded into the catheter which runs through the balloon material all the way through the shaft of the catheter and can be pulled like a ripcord and mechanically deflate the balloon in the event of a non-deflating balloon due, e.g., to crystallization or valve malfunction. In some embodiments, use of this feature eliminates the need for percutaneous or endoscopic balloon puncture or the possible instillation of chemical irritants to deflate the balloon, all of which can cause potential harm to patients. This feature allows the mechanically deflated balloon and the urinary catheter to be removed as one unit.

Without wishing to be bound by any theory, it is believed that the medically appropriate way to insert a urethral catheter in a male is to "hub" the proximate end of the catheter (e.g., the proximate ends of the ports at the urethral meatus). Otherwise there is potential to inflate the balloon within the urethra. By this method, the catheter is inserted far enough to offer reasonable assurance that the urethra, prostate (in a male) and the like have been transited, and that the fluid inlet and retention balloon are safely present within the bladder. Accordingly, in certain embodiments of any of the catheters disclosed herein, one or more markings ("insertion indicia") are included on the safety catheter. Insertion indicia on the catheter, such as a colored (e.g., red, yellow and the like) line, circle, arrow or other distinctive shape or design, denote how far the catheter should be inserted prior to inflation. Insertion indicia can be applied or affixed to the catheter during manufacture or subsequent to manufacture. For example, insertion indicia can be applied (e.g., painted) on the surface of the catheter after manufacture. Accordingly, in some embodiments when a marking is disposed near the urethral meatus, the retention balloon can be inflated with reasonable assurance that the retention balloon is within the bladder. A marking for insertion can also indicate inappropriate (e.g., insufficient) insertion amount for a catheter. Further to all embodiments including a marking described herein, in some embodiments the marking includes or further includes written text, e.g., "Urethral meatus to reach here." Such written text can be in any language and can incorporate abbreviations, numerals, and the like.

Figure 6:
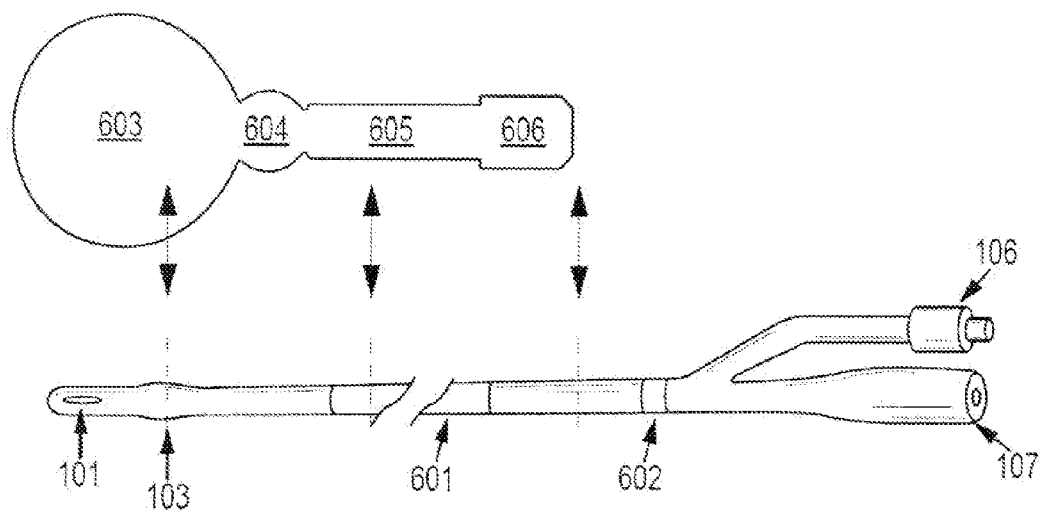
FIG. 6 depicts the positioning of indications of proper insertion amount for some embodiments of the catheter described herein. Element 601 should generally not be visible once the catheter has been inserted to the proper position. Element 601 can be rendered in a warning color (e.g., red, yellow and the like). Element 602 indicates proper insertion amount and can be rendered in a color (e.g., green) to indicate that proper insertion positioning has been achieved. Elements 603-606 are outlines representing the bladder, prostate, penis-urethra and glans, respectively, of a male subject. Vertical double header arrows indicate corresponding positions. Elements 101, 103, 106 and 107 are as defined in FIG. 1.

An exemplary marking is depicted in FIG. 6, which depicts the positioning of markings for proper insertion amount for catheters described herein. When visible, marking 601 (FIG. 6) indicates that a catheter has not been inserted sufficiently to provide reasonable assurance that the retention balloon is within the bladder. Accordingly, marking 601 should generally not be visible once the catheter has been inserted to the proper position. Marking 601 can be rendered in a warning color (e.g., red, yellow and the like), with a warning pattern (e.g., solid, striped, checked, and the like), and/or can include written text (e.g., "Insufficient insertion"). In some embodiments, a marking for insufficient insertion amount is a plurality of markings, e.g., for an adult male, an adult female, a male child or a female child. In some embodiments, a universal marking 601 for adults is used, as described herein. In some embodiments, a universal marking 601 for children is used, as described herein. In some embodiments, each of the plurality of markings is rendered in a different color, different warning pattern, and/or includes appropriate written text. In some embodiments, a catheter of sufficient length for use in an adult includes markings making it useful for use with a child. After insertion of the catheter, marking 601 can alert the subject or medical personnel, upon appearance of marking 601, in the event of a problem, e.g., migration of the catheter. Accordingly, if the catheter has migrated such that marking 601 appears, the subject or medical personal can be advised that a problem exists requiring, e.g., repositioning of the catheter.

Marking 602 indicates proper insertion amount and can be rendered in a color (e.g., green), distinctive pattern, and/or with written text to indicate that proper positioning has been achieved. In some embodiments, marking 602 is located adjacent to the bifurcation in the proximal end of the catheter, as described herein. In some embodiments, marking 602 is located at the bifurcation in the proximal end of the catheter, as described herein. It is understood that for an adult female, marking 602 indicating proper insertion amount can be more distal (i.e., closer to the retention balloon) than generally understood as necessary for an adult male. Without wishing to be bound by any theory, it is believed that there is generally no harm in advancing a catheter further into a female than a male, as long as the retention balloon resides within the bladder. Accordingly, in some embodiments there is provided a marking (e.g., marking 602) useful as a universal marking indicating sufficient insertion amount for both adult males and adult females. Similarly, in some embodiments there is provided a universal marking indicating sufficient insertion amount for both a male child and a female child.

Notwithstanding the belief that no harm may generally attend advancing a catheter further into a female than a male, the length to which a urethral catheter must be inserted in a female to offer reasonable assurance that the urethra has been transited, and that the fluid inlet and retention balloon are safely present within the bladder of the female, can differ from the length of insertion appropriate for a male. Accordingly, in some embodiments, there is provided insertion indicia as described herein denoting how far the catheter should be inserted prior to inflation in a female. In some embodiments, the placement of the insertion indicia described above is appropriate for an adult. In some embodiments, the placement of the insertion indicia described above is appropriate for a child. In some embodiments, the placement of the insertion indicia described above is appropriate for an adult male, an adult female, a male child or a female child.

Kits

In another aspect, there is provided a kit. The kit includes a catheter as disclosed herein and a safety syringe for filling the retention balloon. In some embodiments, a kit is provided including a catheter disclosed herein and one or markings that may be affixed to the catheter.

In some embodiments of the kits described herein, the safety syringe is pre-filled with sterile water. In some embodiments, the safety syringe is adapted to be incapable of applying pressure in excess of a physically harmful inflation pressure. Exemplary safety syringes adapted to be incapable of applying pressure in excess of a defined pressure are known in the art. For example, an exemplary safety syringe is provided in U.S. Pat. No. 6,086,559.

EXAMPLES

Example 1

National Incidence and Impact of Non-Infectious Urethral Catheter Related Complications on the Surgical Care Improvement Project Introduction. Urethral catheterization is performed for many surgical procedures. Indeed, catheter associated urinary tract infections have been targeted by the Joint Commission and the Centers for Medicare and Medicaid Services (CMS) as "Never Events" as known in the art. No regulatory organization, however, has studied, or sought to improve, non-infectious urethral catheter related morbidity caused by these ubiquitous devices.

Noninfectious urethral catheter related complications, referred to as catheter related complications, are a patient safety issue that has received little national attention, although they are well documented in the medical literature. See e.g., Sellett T., 1971, *JAMA* 217:1548; Buddha, S., 2005, *Lancet* 365:909; Kashefi, C., et al., 2008, *J Urol* 179:2254; Thomas, A. Z., et al., 2009, *BJU Int* 104:1109. Catheter related complications comprise a slew of accidental urethral injuries experienced by patients at the hand of the medical practitioner or the patients themselves. For the most part these events may be prevented, not unlike venous line infections or patient falls, by heeding to protocols through training Kashefi et al found the rate of catheter related complications at their institution to be 0.3% for male ward patients. See e.g., Kashefi, C., et al., 2008, Id. This number decreased (but did not disappear) to 0.07% after an educational intervention directed at nurses. However, unlike most other specialized medical/surgical devices, urethral catheters are placed by virtually all health professionals (e.g., ward and operating room nurses, medical students, residents and attendings) whose medical training and experience can vary substantially, making intensive training more difficult.

In addition, accidental dislodgement of an inflated urethral catheter from the bladder, another type of catheter related complication, is estimated to occur in 5% of the intensive care unit population who are more likely to have altered mental status. See e.g., Lorente, L., et al., 2004, *Crit Care* 8:R229. While these rates seem small, when one considers that the prevalence of urethral catheterization is greater than eight million people annually, or approximately 12% to 25% of all patients admitted to a United States hospital, the number of patients potentially affected is actually quite large. See e.g., Saint, S. & Chenoweth, C. E., 2003, *Infect Dis Clin North Am* 17:411.

As members of a consulting urology service based in a tertiary care urban hospital, we are aware of the ongoing incidence and deleterious effects of catheter related complications. A concerted effort to reduce the number of such events will require, at a minimum, an estimation of the baseline incidence rate, for which data are lacking. Furthermore, to motivate regulatory agencies to track this problem, which has not been done to our knowledge at any institution, it is useful to be able to describe the impact of such events on the health care system. One such regulatory body is the Joint Commission, which monitors the quality of care for 7 surgical inpatient procedures through the SCIP (major vascular surgeries, CABG and nonCABG cardiac surgeries, hysterectomy, colon, hip and knee surgeries). Therefore, we assessed whether catheter related complications significantly impacted LOS, urinary tract infection and/or inpatient mortality in the SCIP.

Methods and Materials

Data & Sample. We performed a cross-sectional study of United States patients identified through the 2007 NIS undergoing 1 of the 7 surgical procedures currently monitored through the Joint Commission's SCIP. The NIS is a database of inpatient discharge abstracts collected via federal-state partnerships as part of the Agency for Healthcare Research and Quality Healthcare Cost and Utilization Project. See e.g., INTRODUCTION TO THE HCUP NATIONWIDE INPATIENT SAMPLE (NIS), Rockville, Md.: Agency for Healthcare Research and Quality Healthcare Cost and Utilization Project 2006-2007. The 2007 NIS contains records of discharges from United States, nonfederal hospitals located in 40 states. This approximates a nationally representative 20% stratified sample of United States nonfederal hospitals (representing a total number of 39,541,948 discharges).

The NIS data include patient discharge records, including the data elements for LOS, diagnosis codes and death. From the NIS, data for inpatient urethral catheter related trauma were extracted from patients undergoing surgical procedures for which SCIP performance is specifically reported, including coronary artery bypass grafting, major vascular surgery (aneurysm repair, thromboendarterectomy, vein bypass), hip and knee arthroplasty, hysterectomy, other cardiac surgery and colon surgery. Although no variable exists in the NIS to confirm that a urethral catheter was placed, all of these procedure types are highly likely to involve urethral catheterization at surgery. We identified cases using ICD-9-CM codes listed under the primary procedure for each hospital admission via a method defined by the Joint Commission. See e.g., QUALITY NET: SPECIFICATIONS MANUAL FOR NATIONAL HOSPITAL QUALITY MEASURES, version 2.1, vol 2009, 2006. Patients younger than 18 years old (3,458) were excluded from study since they are not included in SCIP performance measures. Patients were also excluded from study if outcomes data were not available (no length of stay for 3 patients).

Noninfectious urethral catheter related complications were identified through ICD-9-CM diagnostic codes for urethral false passage (599.4), mechanical injury due to indwelling catheter (996.31), other mechanical complication due to genitourinary device (996.39), other complications due to genitourinary device, implant and graft (996.76), and surgical misadventure as a result of urethral catheterization (E879.6). Specific ICD-9-CM diagnostic codes exist for infectious urethral catheter related complications but were not the focus of this study.

Analysis & Statistics. We used weighted hospital discharge rates to calculate the national incidence of noninfectious urethral catheter related complications during each surgical procedure. We then used the Student t test to examine whether a binary variable (noninfectious urethral catheter related event) and a continuous variable (LOS) had any relationship. A chi-square analysis was used to determine if catheter related complications had an association with UTI, inpatient death, gender or the nature of the surgical procedure being performed (elective vs. emergency).

Multivariate analysis was then performed with linear and logistic regression, respectively, to consider patient variables such as age categorized by decade, gender, comorbidities and type of admission (emergency vs. elective) in the determination of whether confounding explained the results of our univariate analysis. Comorbidities were defined in the severity file by the Elixhauser classification, which is a well cited system used in calculating risk adjusted mortality rates. See e.g., Elixhauser, A., et al., 1998, *Med Care* 36:8.

A 2-sided significance level of 0.05 was used for all hypotheses tests with a 95% CI. Size effect was reported and all analyses were performed using Stata/SE® version 10.0 software. This study was exempt from institutional review board review as no patient identifiers are listed in the NIS.

Results

Figure 7:
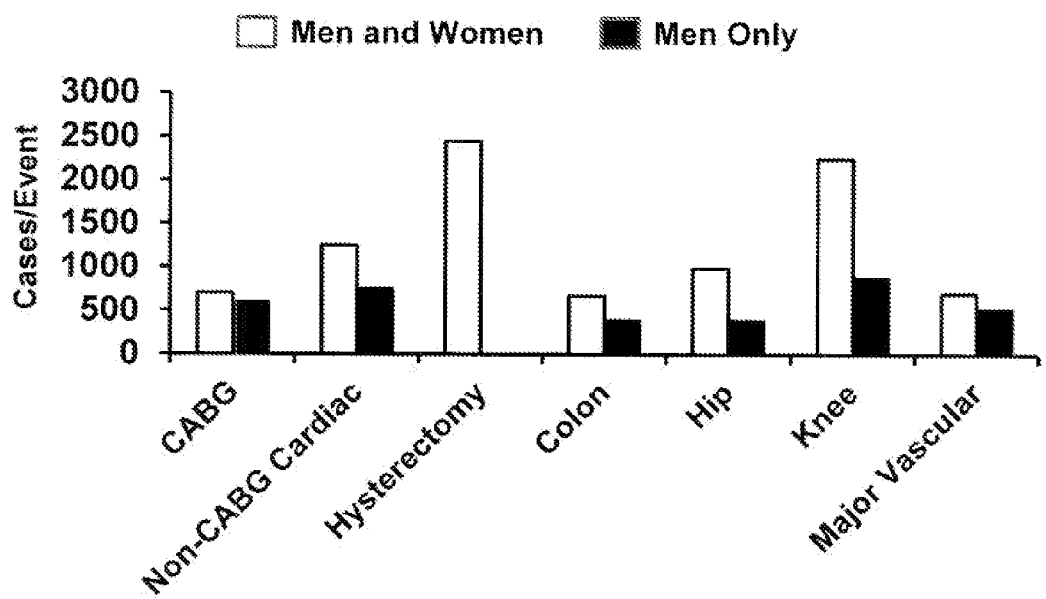
FIG. 7 depicts a histogram showing the 2007 National incidence of urethral catheter related trauma for patients undergoing the seven surgical procedures monitored through the Surgical Care Improvement Project. For each category (x-axis) the entries are Men and Women (left histogram) and Men Only (right histogram).

Incidence and Characteristics. A total of 416,389 cases (representing 2,036,816 cases nationally) were performed in the 2007 NIS for all of the 7 surgical procedures examined. There were 288 cases (representing 1,420 cases nationally) of urethral catheter related complications identified. Surgical case volume, number of catheter related complications, mean age and the percentage of male to female patients treated with each procedure type are listed in Table 1. On average noninfectious urethral catheter related complications occurred in older patients (62 vs. 68 years old, p<0.0001). Of urethral catheter related complications 71% occurred in men vs. women for all procedures despite the fact that 64% of the surgeries were performed in women. They occurred in 0.14% vs. 0.03% of males and females, respectively (p<0.0001). They were more likely to occur (0.12% vs. 0.05%, p<0.0001) if the case was emergency vs. elective. The incidence of urethral catheter related complications ranged from 1 in 685 (major vascular surgery) to 1 in 2,467 (hysterectomy) patients depending on procedure type. See FIG. 7. If women were excluded from analysis then the incidence increased to 1 in 441 (colon surgery) to 1 in 888 (knee surgery).

Analysis. Mean LOS, UTI and death rate are shown in Table 2 for each surgical procedure type with or without a noninfectious urethral related complication. Univariate analysis showed that mean LOS was statistically increased for all surgical procedures except nonCABG cardiac surgery, which still trended toward an increased LOS (11.7 vs. 15.1 days, p<0.10). The increased mean LOS was more than a day and a half for the other 6 procedures (range 1.5 to 3.0 days, p<0.05).

TABLE 2

Univariate analysis of non-infectious urethral catheter related complication on mean length of stay, total charges, and inpatient mortality.

| | Urethral Catheter Related Complication | | |
|---|---|---|---|
| | absent− | present+ | p-value |
| CABG | | | |
| Mean Days LOS | 9.3 | 11.7 | 0.02 |
| UTI (%) | 5.1 | 11.1 | 0.08 |
| Mortality Rate (%) | 1.9 | 2.2 | 0.98 |
| Non-CABG Cardiac | | | |
| Mean Days LOS | 11.7 | 15.1 | 0.22 |
| UTI (%) | 7.3 | 7.1 | 0.95 |
| Mortality Rate (%) | 4.8 | 0.0 | 0.22 |
| Hysterectomy | | | |
| Mean Days LOS | 2.6 | 4.3 | <0.001 |
| UTI (%) | 1.2 | 9.9 | <0.001 |
| Mortality Rate (%) | 0.1 | 0.0 | 0.81 |
| Colon | | | |
| Mean Days LOS | 9.8 | 12.5 | 0.004 |
| UTI (%) | 6.7 | 13.6 | 0.015 |
| Mortality Rate (%) | 3.8 | 2.7 | 0.35 |
| Hip | | | |
| Mean Days LOS | 4.6 | 6.8 | 0.001 |
| UTI (%) | 7.7 | 16.7 | 0.02 |
| Mortality Rate (%) | 0.9 | 1.5 | 0.64 |

TABLE 1

2007 National patient demographics for those undergoing the seven surgical procedures monitored through the Surgical Care Improvement Project.

| | CABG | Non-CABG Cardiac | Hysterectomy | Colon | Hip | Knee | Major Vascular |
|---|---|---|---|---|---|---|---|
| No. Urethral Catheter Related Complications | 50 (0.13) | 11 (0.06) | 31 (0.03) | 77 (0.13) | 57 (0.08) | 39 (0.03) | 24 (0.13) |
| Case Number | 38,926 | 18,493 | 96,593 | 60,620 | 71,403 | 111,752 | 18,360 |
| Age (stdev.) | 65 (11) | 67 (14) | 47 (12) | 64 (16) | 70 (14) | 66 (10) | 68 (12) |
| Male (%) | 73% | 58% | 0% | 48% | 39% | 36% | 63% |
| Mean days LOS | 9.3 | 11.7 | 2.6 | 9.8 | 4.6 | 3.6 | 7.4 |
| % UTI | 5.1 | 0.1 | 1.2 | 7.0 | 7.7 | 2.5 | 3.3 |
| % Elective | 47.0 | 63.0 | 90.0 | 59.0 | 67.0 | 94.0 | 72.0 |
| % Mortality | 1.9 | 4.8 | 0.1 | 3.8 | 0.9 | 0.1 | 3.3 |

Abbr: stddev = Standard deviation.

TABLE 2-continued

Univariate analysis of non-infectious urethral catheter related complication on mean length of stay, total charges, and inpatient mortality.

| | Urethral Catheter Related Complication | | |
|---|---|---|---|
| | absent− | present+ | p-value |
| Knee | | | |
| Mean Days LOS | 3.6 | 5.1 | <0.001 |
| UTI (%) | 2.5 | 10.1 | 0.01 |
| Mortality Rate (%) | 0.1 | 0.0 | 0.8 |
| Major Vascular | | | |
| Mean Days LOS | 7.4 | 10.4 | 0.045 |
| UTI (%) | 3.3 | 15.1 | 0.01 |
| Mortality Rate (%) | 3.3 | 8.6 | 0.29 |

Abbreviations:
LOS, length of stay;
UTI, urinary tract infection;
CABG, coronary artery bypass graft Rates of catheter associated UTI were statistically increased for 5 of the 7 procedures, with an absolute increase ranging from 6.9% to 11.8% (p<0.05). CABG and nonCABG cardiac surgery did not have significant increases in UTI rates for those with catheter related complications. Inpatient mortality rate did not show a statistically significant difference for any of the 7 surgical procedures examined if a patient did or did not experience catheter related complications.

Figure 8:
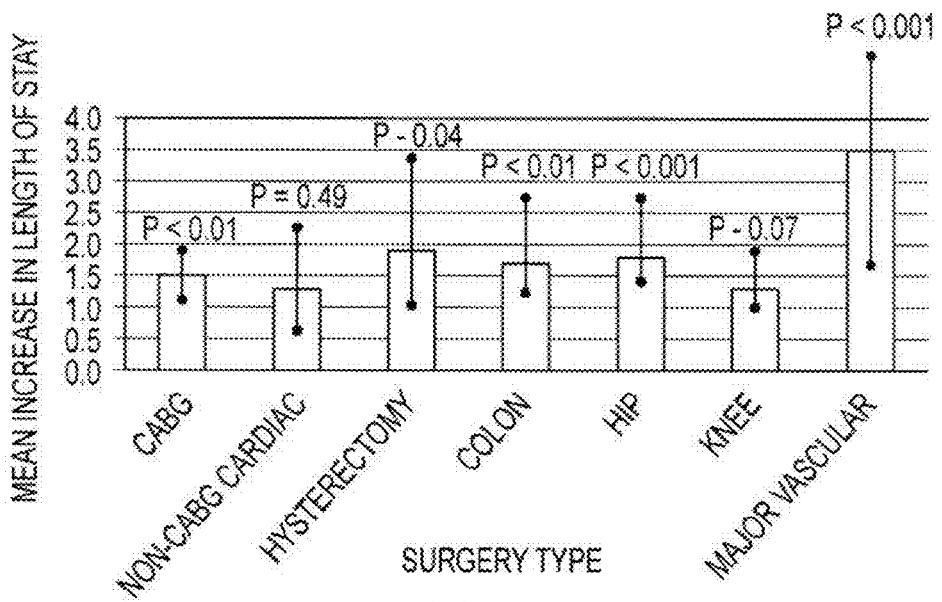
FIG. 8 depicts a histogram showing multivariable analysis of non-infectious urethral catheter related complication on mean length of stay (LOS). The analysis was controlled for patient demographics (age category, race, gender), admission type (elective vs. emergent), and co-morbidities.

Using multivariable linear regression analysis, accounting for patient demographics (age category, race, gender, comorbidities) as well as admission type (elective vs. emergency), LOS was statistically increased for all surgical procedure types except nonCABG cardiac and knee surgery (FIG. 8). The remaining 5 surgical procedures resulted in increased LOS greater than 1 day after controlling for other confounders (range 1.5 to 3.5 days, p<0.05).

Figure 9:
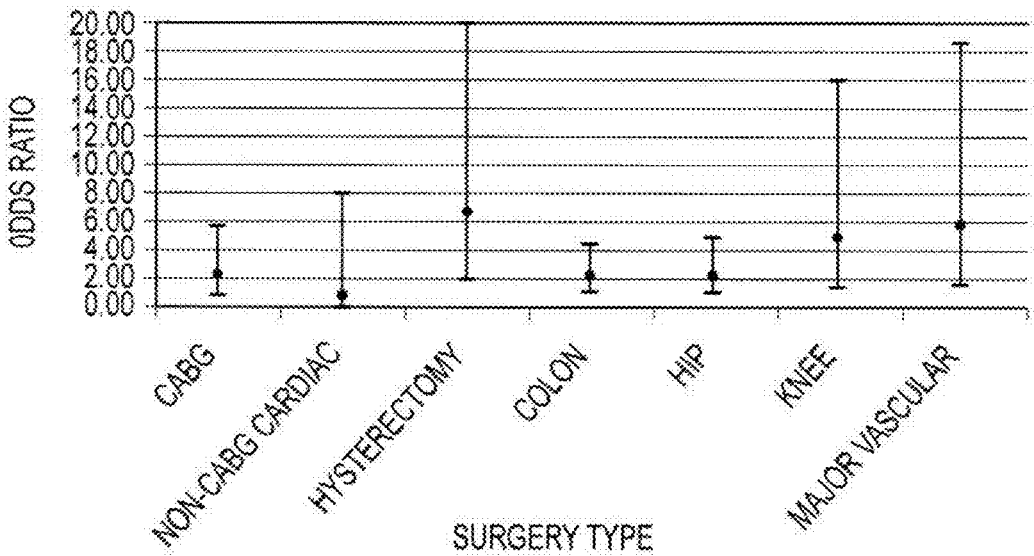
FIG. 9 depicts a histogram showing multivariable analysis of non-infectious urethral catheter related complication on urinary tract infection. Odds ratio with bar represents 95% confidence interval (CI). The analysis was controlled for patient demographics (age category, race, gender), admission type (elective vs. emergent), and co-morbidities.

Using multivariable logistic regression we found no increase in mortality for patients with a noninfectious urethral catheter related complication for any of the 7 procedure types. However, patients with catheter related complications had an increased odds ratio for the development of UTI for 6 of 7 procedure types (OR 2.5 to 6.8, p<0.05, FIG. 9). Only non-CABG cardiac surgery did not have an increased odds ratio for UTI, but trended in that direction (OR 1.06, 95% CI 0.14-8.14, p=0.06).

Discussion

Urethral catheterization is a moderately invasive intervention commonly performed in hospitalized patients that results in a number of noninfectious complications, primarily from iatrogenic trauma or device malfunction. See e.g., Sellet, T., 1971, Id.; Samore, M. H., et al., 2004, *JAMA* 291:325. To date, noninfectious complications associated with urethral catheterization, other than nosocomial urinary tract infection (considered by CMS as never events), are not a target of quality improvement measures or efforts, although we believe that they are just as preventable. We examined the incidence of these complications using a nationally representative administrative data set for 2007 in patients undergoing the 7 surgical procedures currently monitored for quality by the Joint Commission and CMS. Extrapolating from our data we estimated an incidence of 10 to 15,000 noninfectious urethral catheter related complications per year. While this may occur infrequently at any individual hospital, our data suggest that the total number in the United States alone is likely large.

These data reflect the associated effects of catheter related complications within a given hospital stay and, as such, we found that mean LOS and urinary tract infections increased in univariate and multivariate analysis for most of these surgical procedure groups. However, long-term consequences of catheter related complications such as urethral stricture, formation added outpatient costs, bleeding, pain and decreased patient satisfaction, were not examinable in the NIS. One of the goals of this study was to stimulate the interest of an integrated health care system to collect this type of data.

Not surprisingly our findings indicate that older men are at highest risk for this complication, especially when admitted emergently to the hospital. We believe that this group of higher risk individuals warrants special consideration when undergoing urethral catheterization. Perhaps more experienced individuals should perform the procedure rather than novice trainees and/or the standard hospital catheter should be substituted for a larger Coude catheter in anticipation of confronting an enlarged prostate. The one size fits all mentality for the placement of a urethral catheter may be cheaper for the hospital, but is not a rational policy. Imagine if every patient regardless of size received a standard ureteral stent.

Why these noninfectious urethral catheter related complications occur has been examined in a study showing that undertrained health care professionals have a role and that a nurse training program can reduce them. See e.g., Kashefi, C., et al., 2008, Id. However, not all urethral catheters are placed by nurses, and in fact many other health care professional share this responsibility. See e.g., Thomas, A. Z., et al., 2009, Id. Patient factors such as urethral/prostate anatomy and prior pelvic surgery/radiation also may lead to urethral catheter related complications. See e.g., Beaghler, M., et al., 1994, Urology 44:268.

Self-removal in the altered patient is another source of preventable catheter related complications. Not unlike preventing falls in the hospital, deemed a never event by CMS, we should minimize the causes of altered mental status or identify them more quickly so that appropriate supervision of the patient occurs to prevent catheter dislodgement. In addition, catheters should be properly secured to prevent accidental traction and dislodgement even in the alert patient.

Finally, and perhaps most importantly, the medical devices that interface with the patient also have an important role in maintaining patient safety and quality of care, and the design of the urethral catheters itself is of paramount importance. Just as safety features have become a part of other everyday medical devices (intravenous kits, scalpels etc), there should be more efforts to make urethral catheters inherently safer devices for a health professional to place and for a patient to use, so as to prevent or mitigate urethral catheter related complications. The authors would start with the appropriate labeling of catheters so that undertrained personal can avoid pitfalls such as filling a 5 cc balloon with 5 cc or using saline instead of water. Underfilling the balloon reduces the force necessary to dislodge a urethral catheter from the bladder into the urethra (data submitted for publication).

There are some limitations to this study. The retrospective nature of our study and the means through which the administrative data were collected are known limitations. We strongly believe that our work merely illustrates the minimum incidence and impact of catheter related complications in patients treated in the acute care setting for these 7 surgical procedures. More work will be necessary to examine other patient populations, including other disease states/procedures and that in the nursing home where urethral catheter use is highest.

Ultimately we hope to raise awareness of these types of complications as we believe that they occur much more frequently than is reported, and we certainly do not wish to imply that our findings justify the apparent ongoing disinterest in this patient safety issue. We also wish to draw attention to the fact that noninfectious urethral catheter related complications are a potentially significant patient safety issue, associated with severe long-term consequences for the patient, an increased LOS and an increased rate of urinary tract infections. See e.g., Gleckman, R., et al., 1982, *J Am Geriatr Soc* 30:255. Most importantly the potential noninfectious morbidity of the urinary catheter can be mitigated by the recognition of these risks and the implementation of focused strategies to promote safe use such as adequate training, appropriate catheter selection and potentially spurring manufactures to create a safer urethral catheter.

However, we acknowledge that noninfectious urethral catheter related complications are reported infrequently for the seven surgical procedures monitored by SCIP in this nationally representative administrative data set. Yet catheter related complications are associated with an increased LOS and rate of UTI for most procedure types in multivariable analysis. Despite the relatively low incidence of this complication, due to the sheer number of patients undergoing urethral catheterization, noninfectious urethral catheter related complications do represent a significant patient safety issue that can be prevented.

Example 2

Catheter Pressure and Force Studies

Objectives

The urethral catheter is ubiquitous in medical care. A urethral catheter is inserted in nearly 25% of all hospitalized patient. See e.g., Haley, R W, et al., 1981, *Am J Med* 70:947-959. Unlike other medical devices, all levels of healthcare professionals from doctors to nursing trainees place urinary catheters. See e.g., Thomas. A Z, et al., 2009, *BJU Int*, 104: 1109-1112; Saint, S. & Lipsky, B A., 1999, *Arch Intern Med*, 159:800-808. National healthcare efforts have focused on reducing the incidence of catheter related urinary tract infections which have been deemed a "never event" by the Centers for Medicare and Medicaid Services. See e.g., Wald, H L, et al., 2008, *Arch Surg*, 143:551-777. However, catheter related iatrogenic injuries receive little attention despite the observation that an estimated 0.3% of hospital patients suffer catheter placement injuries. See e.g., Kashefi, C., et al., 2008, *J Urol*, 179:2254-2257; discussion 2257-2258. Additionally, accidental removal of an urethral catheter with a filled balloon is estimated to occur in 5% of intensive care unit patients. See e.g., Lorente, L., et al., 2004, *Crit Care*, 8:R229-233. Iatrogenic urethral catheter injury represents a significant safety issue that warrants further investigation as it can cause pain, severe bleeding, urethral stricture, and need for surgical intervention.

Iatrogenic catheter-related urethral injury occurs by a variety of mechanisms. In order to identify ways to prevent catheter-related injuries, we focused on the two main mechanisms: catheter placement and removal. Significant urethral injury can occur when the catheter balloon is inappropriately filled in the relatively non-distensible urethra or when the filled catheter balloon is accidentally pulled out of the bladder. See e.g., Lorente, L., et al., 2004, Id.; Sellett, T., 1971, *JAMA*, 217:1548-1549; Buddha, S., 2005, *Lancet*, 365:909.

The force used to place urethral catheters has been studied in an ex vivo model, but, it is believed that no study has shown force and pressure measurements associated with urethral catheter injury. See e.g., Canales, B K, et al., 2009, *Int Braz J Urol* 35:84-99; discussion 89. We hypothesize that urethral catheter balloon pressures are greatly increased when the balloon is filled within the urethra versus the bladder. Also, we hypothesize that withdrawal of a filled catheter balloon from the bladder into the urethra requires significant force. Our aim is to design a safer urethral catheter to prevent unnecessary patient harm.

Methods and Materials.

Intra-Urethral Inflation Studies Using an Ex-Vivo Model of Urethra. Studies were conducted using a mock urinary bladder neck and urethra, using a rigid plastic funnel connected to a well lubricated 30 Fr semi-rigid tube. 16 Fr latex catheters with 5 cc retention balloons (Allegiance, USA; recommended fill volume: 10 cc), 16 Fr silicone catheters with 5 cc retention balloons (Rochester Medical, USA; recommended fill volume 10 cc), and 22 Fr latex catheters with 30 cc retention balloons (Allegiance, USA; recommended fill volume 35 cc) were used. Pressure within the balloon was measured using a pressure gauge (Marsh Pressure Gauge, Marshall Instruments, Inc., Anaheim, Calif.) attached to the catheter balloon filling-port. Pressure measurements were recorded initially and at 10 seconds upon filling the balloon within the mock urethra and the mock bladder using 0, 5, 7, and 10 cc of water. The 10 second measurement was added after the catheter system was noted to require time to equilibrate. Care was taken to exclude air from the retention balloon system. All studies were repeated in triplicate; mean result values with standard error of the mean (SEM) are reported.

Intra-urethral Inflation Studies: Cadaver Model. Lubricated 16 Fr latex catheters with 5 cc balloons were inserted per urethra of three fresh male cadavers in standard fashion. See e.g., Thomsen, T W & Setnik, G S, 2006, *N Engl J Med*, 354: e22. Sterile water was used to fill the catheter balloon with 0, 5, and 10 cc in the bladder and at defined locations within the urethra, including the prostatic urethra, the bulbar urethra, and the pendulous urethra. The location was estimated as the catheter was withdrawn past the bladder neck. Pressure within the balloon was recorded when the balloon was filled with each amount of water as described above. The same catheter was used sequentially with deflation of the balloon prior to movement to the next segment of the urethra. If balloon port expansion occurred from high balloon port pressures, then a new catheter was used. Additional measurements were taken with the catheter balloon filled with 0 to 5 cc of water in the fossa navicularis to replicate the pressure effects during retrograde urethrography. Pressure was measured upon initial filling of the balloon and 10 seconds afterward to account for tissue relaxation and system equilibration. Ten seconds after balloon filling, no further changes in balloon pressure were noted (data not shown). The experiments were repeated in a total of three cadavers. Individual cadavers were not used for multiple experiments due to concern that the urethral tissue would be significantly altered by each experiment.

Forced Removal of a Urethral Catheter (Balloon Filled) Per Urethra: Ex-Vivo Model. Studies using our ex vivo model (described above) were performed. Latex and silicone 16 Fr catheters (5 cc balloon) were filled with 5, 7, 10 and 20 cc of sterile water. Latex 22 Fr (30 cc balloon) catheters were filled with 5, 10, 35, and 55 cc of sterile water. The largest volumes instilled represent the common practice of balloon over-filling to reduce post-operative hematuria after surgical procedures such as transurethral resection of the prostate. A force meter (Accu-Scale & Systems Inc, Melrose, Mass.) was used to measure the force required (Pound-Force, Lbs) to remove the catheter from the model of the bladder with the balloon filled at varying amounts. All studies were repeated in triplicate with mean and standard error of the mean (SEM) reported.

Forced Removal of a Urethral Catheter (Balloon Filled) Per Urethra: Cadaver Model. Lubricated 16 Fr latex catheters were placed per urethra in three fresh male cadavers using standard technique. The catheter balloon was filled with 0, 5, 7, and 10 cc of sterile water. After filling to the designated amount, the catheter was forcibly removed. Experimental measurements were performed as describe above for studies using the ex vivo model. After force measurements were obtained for removal with 10 cc of fill, the cadaver was not used again out of concern that the bladder neck would be significantly altered by catheter balloon removal. Experimentation was repeated in 3 cadavers. All cadavers were obtained by the University of California, San Francisco, Orthopedic Surgery department by voluntary donation for the purpose of medical training and research.

Results

Pressure Associated with Filling the Balloon in the Urethra. The catheter balloons, free of external constriction, had good compliance. For all catheters (varying by material type and balloon volume), balloon pressures within the model bladder averaged 59 kPa (±2 kPa). Balloon pressures in the bladder model, using a 16 Fr latex catheter, increased from an average 63 kPa (±2 kPa) to 67 kPa (±3 kPa) with 5 cc to 20 cc of fluid, respectively. In the ex vivo model, silicone catheters and the larger latex catheters also showed relatively stable balloon pressures with increasing fill volumes within the model bladder. See Table 3.

TABLE 3

Balloon pressure in the ex vivo model at various states of filling and using different catheter types. Percent change in pressure from bladder to urethra model is shown in rightmost column. (1 kPa = 0.0099 atm = 0.15 psi = 7.5 mmHg).

|  | Balloon Filling Volume (cc) | Pressure in bladder model (kPa w/ std dev) | Pressure in urethra model (kPa w/ std dev) | % Change |
|---|---|---|---|---|
| 16F Latex 5 cc balloon | 0 | 0 (0) | 0 (0) | 0 |
|  | 5 | 63 (2) | 182 (21) | 287 |
|  | 7 | 62 (2) | 183 (17) | 297 |
|  | 10* | 63 (3) | 173 (15) | 274 |
|  | 20 | 67 (4) | 167 (9) | 250 |
| 16F Silicone 5 cc balloon | 0 | 0 (0) | 0 (0) | 0 |
|  | 5 | 47 (9) | 207 (30) | 443 |
|  | 7 | 48 (9) | 210 (24) | 435 |
|  | 10* | 50 (10) | Balloon Burst | NA |
|  | 20 | 53 (6) | Balloon Burst | NA |

TABLE 3-continued

Balloon pressure in the ex vivo model at various states of filling and using different catheter types. Percent change in pressure from bladder to urethra model is shown in rightmost column. (1 kPa = 0.0099 atm = 0.15 psi = 7.5 mmHg).

|  | Balloon Filling Volume (cc) | Pressure in bladder model (kPa w/ std dev) | Pressure in urethra model (kPa w/ std dev) | % Change |
|---|---|---|---|---|
| 22F Latex 30 cc balloon | 0 | 0 (0) | 0 (0) | 0 |
|  | 5 | 73 (7) | 212 (9) | 289 |
|  | 10 | 68 (3) | 177 (12) | 265 |
|  | 35* | 60 (0) | 137 (9) | 228 |
|  | 55 | 57 (3) | 137 (9) | 241 |

Legend:
* is manufacturer-recommended balloon filling volume.
Abbreviations:
NA, not applicable;
SEM, standard error of mean.

Balloon pressures within the mock urethra averaged 177 kPa (±6 kPa), about 3 times higher, than in the mock bladder model across catheter types with 10 cc of fill. At balloon fill volumes of 7 cc, within the mock urethra, the neck of the balloon filling port expanded preferentially. Furthermore, balloon pressure did not increase in a linear fashion with filling volumes greater than 7 cc because the neck of the balloon port shunted the excess pressure. Using the 16 Fr latex catheter, maximal pressure was achieved when the balloon was filled with 5 cc fluid volume (mean 182 kPa, ±21 kPa); when the balloon was filled with 20 cc of fluid, mean maximal pressure was only 167±9 kPa. Balloon filling with greater volumes than the threshold pressure level resulted in continued balloon port expansion, not increasing intra-balloon pressure. Similar results were found with 22 Fr latex catheters (30 cc balloon), although the threshold fill volume at which we noted balloon port expansion was 10 cc. Silicone catheters did not perform in a similar fashion: as the balloon was filled within the urethra, the balloon port did not expand to serve as a "pop-off" valve. Rather, when the balloon was filled with >7-10 cc of water, the balloon ruptured within the mock urethra. See Table 3.

Identical experiments in the male cadavers yielded similar results. Balloon pressures within the urethra were nearly two times higher than within the bladder (Table 4), and, in all measurements (within the bladder and in various locations within the urethra), balloon pressure was always highest immediately upon filling, and slightly lower 10 seconds after filling, presumably due to relaxation of the cadaveric tissue and balloon port neck expansion. Mean balloon filling pressure was highest within the penile urethra (~2.2× bladder), followed by the bulbar (~2.0× bladder) and prostatic (~1.6× bladder) urethra with 10 cc. See Table 4.

TABLE 4

Balloon pressures upon filling a 5 cc balloon of a latex catheter in different locations (prostatic, bulbar, and penile urethra) of the cadaver model. The balloon was filled with either 5 cc or 10 cc sterile water. Pressure was measured both immediately after filling and after 10 seconds, to allow system equilibration. Percent change in pressure from the bladder after 10 seconds is shown in the third and rightmost column. Standard error of the mean (SEM) is shown in parentheses.

|  | 5 cc | | | 10 cc | | |
|---|---|---|---|---|---|---|
|  | Immediate (kPa w/std. dev.) | After 10 sec (kPa w/std. dev.) | % change from bladder after 10 sec | Immediate (kPa w/std. dev.) | After 10 sec (kPa w/std. dev.) | % change from bladder after 10 sec |
| Bladder | 95 (3) | 65 (8) | NA | 97 (3) | 68 (4) | NA |
| Prostatic Urethra | 130 (38) | 110 (21) | 169 | 178 (38) | 112 (19) | 164 |

TABLE 4-continued

Balloon pressures upon filling a 5 cc balloon of a latex catheter in different locations (prostatic, bulbar, and penile urethra) of the cadaver model. The balloon was filled with either 5 cc or 10 cc sterile water. Pressure was measured both immediately after filling and after 10 seconds, to allow system equilibration. Percent change in pressure from the bladder after 10 seconds is shown in the third and rightmost column. Standard error of the mean (SEM) is shown in parentheses.

| | 5 cc | | | 10 cc | | |
|---|---|---|---|---|---|---|
| | Immediate (kPa w/std. dev.) | After 10 sec (kPa w/std. dev.) | % change from bladder after 10 sec | Immediate (kPa w/std. dev.) | After 10 sec (kPa w/std. dev.) | % change from bladder after 10 sec |
| Bulbar Urethra | 147 (15) | 120 (25) | 185 | 180 (15) | 140 (21) | 205 |
| Penile Urethra | 165 (9) | 132 (2) | 204 | 183 (19) | 150 (16) | 220 |

Abbreviations:
NA, not applicable;
SEM, standard error of mean.

When the balloon was filled within the fossa navicularis, filling with only 3 cc fluid resulted in a balloon-pressure increase of 145 kPa, which is comparable to that achieved with 3-fold greater filling volume with the balloon in the bulbar urethra, 140 kPa. Expansion of the balloon port was observed in all trials using a latex catheter with balloon filling within the urethra.

Force Required to Withdraw a Catheter from the Bladder.

Experiments using both ex vivo models and fresh male cadavers confirmed that at higher balloon fill volumes, greater manual traction force is required to withdraw the catheter from the bladder. See Table 5. In the ex vivo bladder/urethra model removal of a 16 Fr latex catheter required an average of 2.1 lbs (±0.1 lbs) and 9.3 lbs (±1.8 lbs) traction force when the balloon was filled with 5 cc and 10 cc fluid volume, respectively. Over-filling of the 5 cc balloon with 20 cc fluid required significantly greater (>20 lbs) force, exceeding the measurement threshold of our measurement apparatus. Similar results were noted using a 22 Fr latex catheter (30 cc balloon) filled with >35 cc fluid as a manual traction force >20 lbs was required to withdraw the filled balloon per urethra. Silicone catheters also required greater manual traction force to withdraw the balloon per urethra at higher filling volumes. At balloon volumes >20 cc water, the silicone balloon invariably burst with force greater than 10 lbs.

TABLE 5

Traction force required to dislodge catheter from ex vivo mock bladder and cadaver. Data are shown for various degrees of balloon filling volume, and, using catheters made of different materials (silicone, latex) and of different diameters (16F (French) and 22 F).

| | Balloon Filling Volume (cc) | Force (lbs) | Standard Deviation (lbs) |
|---|---|---|---|
| 16F Latex 5 cc balloon | 0 | 0 | 0 |
| | 5 | 2.1 | 0.1 |
| | 7 | 5.8 | 1.0 |
| | 10* | 9.3 | 3.2 |
| | 20 | >20‡ | — |
| 16F Silicone 5 cc balloon | 0 | 0 | 0 |
| | 5 | 1 | 0 |
| | 7 | 3.5 | 0.4 |
| | 10* | 7.5 | 0.4 |
| | 20 | >10† | — |
| 22F Latex 30 cc balloon | 0 | 0 | 0 |
| | 5 | 1.5 | 0.3 |
| | 10 | 3.7 | 0.4 |
| | 35* | >20‡ | — |
| | 55 | >20‡ | — |
| 16F Latex 5 cc balloon | 0 | 0 | 0 |
| | 5 | 4.5 | 0.5 |

TABLE 5-continued

Traction force required to dislodge catheter from ex vivo mock bladder and cadaver. Data are shown for various degrees of balloon filling volume, and, using catheters made of different materials (silicone, latex) and of different diameters (16F (French) and 22 F).

| | Balloon Filling Volume (cc) | Force (lbs) | Standard Deviation (lbs) |
|---|---|---|---|
| in Cadaver model | 7 | 5.5 | 0.5 |
| | 10* | 10.3 | 0.9 |

Legend:
*Manufacturer-recommended balloon filling volume;
‡Exceeded experimental limit, and catheter could not be removed;
†Balloon burst at this amount of force.

Discussion

Indwelling urethral catheters are commonplace in healthcare settings, and they are inserted into patients by health professionals at all levels of training Incorrect insertion or removal can result in significant patient harm. While incorrect insertion or partial removal can be readily identified, the trauma at this point has already occurred. See e.g., Vaidyanathan, S, et al., 2008, *Cases J*, 1: 43. Unfortunately, incidents of catheter balloon filling within the urethra and accidental catheter removal of an indwelling catheter with the balloon filled continue to be reported in the patient care setting. Though the exact incidence of these problems has not been well studied, two key factors suggest the incidence of these safety-related issues will continue: 1. Catheters are used by such a diverse group of health professionals that rigorous training is a practical challenge; 2. Few modifications to catheter design have occurred within the last 20 years, and such efforts have been primarily limited to mechanisms to reduce catheter related urinary tract infections. See e.g., Schumm, K. & Lam, T B., 2008, *Neurourol Urodyn*, 27:738-746.

Surprisingly, no attention has been placed on how to make catheters safer to insert and use. We sought to define the physical parameters whereby iatrogenic injuries from urethral catheters occur in order to help guide design of a safer device. We found that balloon pressures, when the catheter balloon was filled appropriately within the bladder, varied little and were less than half that seen when filled in the urethra in both the ex vivo and cadaveric model. Interestingly, we discovered that a threshold balloon pressure exists for latex, but not silicone catheters, at which point the neck of the balloon port served as an unrecognized pressure release valve mechanism (albeit set at a level that does not prevent patient harm). The less compliant silicone catheters do not demonstrate this pressure release mechanism as they burst beyond the threshold balloon pressure level. Finally, we found balloon pressures vary in different portions of the urethra with higher balloon pressures demonstrated as the balloon was filled more distally.

For instance, at the fossa navicularis, balloon pressures were similar to those found within the prostatic urethra with much lower balloon filling volumes (3 versus 10 cc). This may help explain the frequent expression of patient discomfort during retrograde urethrography where the urethral catheter is filled in the fossa navicularis.

The second portion of our study showed in both models that increasing force was required to dislodge a urethral catheter from the bladder into the urethra as the balloon fill volume increased. This trend was noted in all catheter sizes and types tested. Interestingly, catheters composed of silicone were the only type to burst their balloon upon forceful removal from the bladder, which reflects the less compliant properties of silicone compared to latex.

It is imperative that healthcare professionals performing urethral catheterization receive appropriate training See e.g., Thomas, A. X., et al., 2009, *BJU Int* 104:1109-1112. A recent study of a training intervention on urethral catheter placement at a single institution significantly reduced the incidence of male urethral trauma. See e.g., Kashefi, C., et al., 2008, *J Urol* 179:2254-2257; discussion 2257-2258. Yet, despite this intervention iatrogenic injuries still occurred. Designing a safer urethral catheter that facilitates healthcare professionals in the placement of the catheter within the bladder would reduce unnecessary patient harm and warrants further exploration. We hypothesize that a catheter that has a thinner wall at the neck of the balloon port, serving as a designed pop-off pressure valve, might provide manufacturers the unique opportunity to inexpensively add a catheter safety mechanism. This mechanism would serve to notify the health professional placing the catheter of the incorrect location of the catheter balloon within the urethra through visual and tactile feedback by expansion of the balloon port. This "second balloon" would also serve to prevent harmful high intra-urethral pressures thereby avoiding urethral rupture, bleeding, pain, and increased length of hospitalization.

This study also addresses the common occurrence of accidental dislodgement of a catheter with a filled balloon from the bladder. An estimated one in twenty ICU patients suffers this event during their hospitalization. See e.g., Lorente, L., et al., 2004, *Crit care* 8:R229-R233. Our study raises the question of whether or not to overfill the catheter balloon to make it more difficult for a patient at higher risk for urethral self-injury to apply sufficient force to dislodge their catheter. However, one caveat is that a larger balloon may cause more urethral damage if a patient was still able to apply sufficient extraction force to remove their catheter.

Additionally, our findings suggest that given the propensity of silicone balloons to burst at high pressures or forces, these catheters might not be ideal for patients with altered mental status who are at higher risk to pull out their catheters. Notwithstanding, intravesical bursting of the catheter balloon may lead to retained catheter fragments with bleeding and trauma from the burst itself necessitating cystoscopic intervention. See e.g., Chrisp, J M. & Nacey, J N., 1990, *Br J Urol*, 66:500-502.

Study limitations include the inability to test all catheter types and sizes in the cadaveric model, and the lack of in vivo data, which would not be ethical. However, ex vivo studies provided us with inferential data as they trended with our findings in the fresh cadavers. We acknowledge that actual pressure and force measurements will change in a living human with perfused tissue, but feel that the data trends and catheter deformation findings would remain constant. We did not design our study for the female population because catheter related injuries are far less common due to the wider and shortened female urethra. The number of repetitions performed in ex vivo experimentation may be considered a limitation, but we feel that the use of highly standardized, high-grade medical catheters negates the need for additional testing. Finally, balloon pressures serve as a surrogate measure of urethral trauma. Certainly, as evidenced by the non-zero filling pressures within the bladder, balloon pressures are related to both the baseline compliance of the catheter balloon material and the amount of pressure exerted on and from surrounding tissue.

Filling of urethral catheter retention balloons within the urethra results in two or more times greater balloon pressures than when filled within the bladder. Catheters with larger balloon filling volumes require greater force to remove from the bladder when filled completely. The differences in balloon pressure found with filling within the urethra versus the bladder, and the force required to remove a catheter with a filled balloon from the bladder, could potentially be exploited to design a safer urethral catheter thereby preventing unnecessary patient harm.

Conclusions

Iatrogenic complications from improper urethral catheter use is common. Catheter balloon pressures and manual extraction forces associated with urethral injury are significantly greater than those found with normal use. The differences in pressure and force may be incorporated into a safer urethral catheter design, which may significantly reduce iatrogenic urethral injury associated with catheterization.

What is claimed is:

1. A catheter comprising:
   an elongated tubular member comprising a proximal end and a distal end;
   a fluid inlet disposed at said distal end in fluid communication with a fluid outlet disposed at said proximal end;
   a first lumen within said elongated tubular member providing fluidic communication between said fluid inlet and said fluid outlet;
   a retention balloon disposed at said distal end;
   a retention balloon filling inlet disposed at said proximal end;
   a second lumen within said elongated tubular member providing fluidic communication between said retention balloon and said retention balloon filling inlet; and
   a marking on said elongated tubular member, said marking disposed at a position indicating proper insertion amount for said catheter;
   a safety balloon in fluid communication with said second lumen, said retention balloon filling inlet and said retention balloon, wherein said safety balloon is disposed distal to said retention balloon filling inlet;
   wherein said elongated tubular member surrounding the second lumen comprises a thinned or scored region of said elongated tubular member thereby forming said safety balloon.

2. The catheter according to claim 1, wherein said thinned or scored region of the elongated tubular member surrounding the second lumen is internal or external to said second lumen.

* * * * *